US012622948B2

(12) United States Patent
Thennati et al.

(10) Patent No.: US 12,622,948 B2
(45) **Date of Patent: *May 12, 2026**

(54) GLP-1/GIP DUAL AGONISTS

(71) Applicant: SUN PHARMACEUTICAL INDUSTRIES LIMITED, Mumbai (IN)

(72) Inventors: Rajamannar Thennati, Vadodara (IN); Vinod Sampatrao Burade, Vadodara (IN); Muthukumaran Natarajan, Vadodara (IN); Dhiren Rameshchandra Joshi, Vadodara (IN); Manish Harendraprasad Gandhi, Vadodara (IN); Chandulal Thakarshibhai Jivani, Vadodara (IN); Abhishek Tiwari, Kota (IN); Krunal Harishbhai Soni, Soni (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/812,797

(22) Filed: Aug. 22, 2024

(65) Prior Publication Data

US 2024/0400613 A1 Dec. 5, 2024

Related U.S. Application Data

(63) Continuation of application No. 18/249,055, filed as application No. PCT/IB2021/059420 on Oct. 13, 2021.

(30) Foreign Application Priority Data

Oct. 17, 2020 (IN) ............................. 202021045240
Jan. 20, 2021 (IN) ............................. 202121002837

(51) Int. Cl.
*A61K 38/26* (2006.01)
*C07K 4/00* (2006.01)
*C07K 14/605* (2006.01)

(52) U.S. Cl.
CPC ................ *A61K 38/26* (2013.01); *C07K 4/00* (2013.01); *C07K 14/605* (2013.01)

(58) Field of Classification Search
CPC ......... A61K 38/26; C07K 14/605; C07K 4/00
See application file for complete search history.

(56) References Cited

U.S. PATENT DOCUMENTS

| | | | |
|---|---|---|---|
| 8,980,581 | B2 | 3/2015 | Wang et al. |
| 11,866,477 | B2 | 1/2024 | Thennati et al. |
| 2016/0199438 | A1 | 7/2016 | Bokvist et al. |
| 2019/0309040 | A1 | 10/2019 | Thennati et al. |
| 2023/0241178 | A1 | 8/2023 | Thennati et al. |
| 2024/0020543 | A1 | 1/2024 | Thennati et al. |
| 2024/0424063 | A1 | 12/2024 | Thennati et al. |

FOREIGN PATENT DOCUMENTS

| | | | |
|---|---|---|---|
| TW | 201636362 | A1 | 10/2016 |
| WO | 2011094337 | A1 | 8/2011 |
| WO | 2013/164483 | | 11/2013 |
| WO | 2013/192129 | | 12/2013 |
| WO | 2015/067715 | | 5/2015 |
| WO | 2016/111971 | | 7/2016 |
| WO | 2017074714 | A1 | 5/2017 |
| WO | 2018136440 | A1 | 7/2018 |
| WO | 2019/193576 | | 10/2019 |
| WO | 2019245893 | A2 | 12/2019 |
| WO | 2020023386 | A1 | 1/2020 |
| WO | 2020023388 | A1 | 1/2020 |
| WO | 2020207477 | A1 | 10/2020 |
| WO | 2021/260530 | | 12/2021 |

OTHER PUBLICATIONS

International Search Report (ISR) with Written Opinion for PCT/IB2021/059420 mailed Jan. 20, 2022, pp. 1-8.
Tamer Coskun et al. "LY3298176, a novel dual GIP and GLP-1 receptor agonist for the treatment of type 2 diabetes mellitus: From discovery to clinical proof of concept" Molecular Metabolism (2018) vol. 18, pp. 3-14.
Yuliantie Elita et al. "Pharmacological characterization of mono-, dual- and tri-peptidic agonists at GIP and GLP-1 receptors" Biochemical Pharmacology (2020) vol. 177, XP086183537.
B. Finan et al. "Unimolecular Dual Incretins Maximize Metabolic Benefits in Rodents, Monkeys, and Humans" Science Translational Medicine (2013) vol. 5(209), pp. 209ra151-209ra151.
Evers Andreas et al. "Dual Glucagon-like Peptide 1 (GLP-1)/Glucagon Receptor Agonists Specifically Optimized for Multidose Formulations" Journal of Medicinal Chemistry (2018) vol. 61(13) pp. 5580-5593.
International Search Report (ISR) and Written Opinion for PCT/IB2021/055457 mailed Oct. 8, 2021.
"Obesity: Obesity and the Metabolic Syndrome: Merck Manual Professional," Merck Manuals, accessed Oct. 6, 2014, 9 Pages, Retrieved from Internet URL: https://www.merckmanuals.com/professional/nutritional-disorders/obesity_and_the_metab?ruleredirectid=210.
"What Causes Overweight and Obesity?," National Heart, Lung, and Blood Institute, accessed Oct. 6, 2014, 5 Pages, Retrieved from Internet URL: https://www.nhlbi.nih.gov/health/health-topics/topics/obe/causes.html.

(Continued)

*Primary Examiner* — Li N Komatsu
(74) *Attorney, Agent, or Firm* — Blank Rome LLP

(57) ABSTRACT

The present invention relates to long acting glucagon-like peptide-1 and human glucose-dependent insulinotropic polypeptide (GIP) dual agonist polypeptide which may be useful for treating type 2 diabetes mellitus (T2D), diabetes with obesity, obesity and hyperlipidemia.

24 Claims, No Drawings

Specification includes a Sequence Listing.

(56) References Cited

OTHER PUBLICATIONS

Marin-Peanlver, J J., et al., "Update on the Treatment of Type 2 Diabetes Mellitus," World Journal of Diabetes, Sep. 2016, vol. 7(17), pp. 354-395.

"Obesity Causes," Harvard School of Public Health, accessed Oct. 6, 2014, 3 Pages, Retreived from URL: https://nutritionsource.hsph.harvard.edu/obesity/.

GLP-1/GIP DUAL AGONISTS

CROSS-REFERENCE TO RELATED APPLICATIONS

This application is a continuation of U.S. patent application Ser. No. 18/249,055, filed Apr. 13, 2023, which is a U.S. National Stage Entry of International Patent Application No. PCT/IB2021/059420, filed Oct. 13, 2021, which claims the benefit of priority of Indian Patent Application No. 202021045240, filed Oct. 17, 2020, and Indian Patent Application No. 202121002837, filed Jan. 20, 2021, each of which is hereby incorporated herein by reference in its entirety.

REFERENCE TO AN ELECTRONIC SEQUENCE LISTING

This application contains a Sequence Listing which has been submitted electronically and is hereby incorporated by reference in its entirety. The Sequence Listing was created on Aug. 22, 2024, is named "23-0315-WO-US-CON_SequenceListing_ST26" and is 44,662 bytes in size.

FIELD OF THE INVENTION

The present invention relates to long acting glucagon-like peptide-1 (GLP-1) and human glucose-dependent insulinotropic polypeptide/Gastro Intestinal Peptide (GIP) dual agonist polypeptides which may be useful for treating type 2 diabetes mellitus (T2D), diabetes with obesity, obesity and hyperlipidemia.

BACKGROUND OF THE INVENTION

Treatment of type 2 diabetes mellitus (T2DM) with glucagon-like peptide-1 receptor agonists (GLP-1RAs) leads to improved glycaemic control, reduced body weight, and improvement in several cardiovascular risk factors. These benefits are mediated by the glucagon-like peptide-1 receptor (GLP-1R), a member of the class B family of G protein-coupled receptors, that is expressed in pancreatic beta-cells, various cell types of the gastrointestinal tract and neurons throughout both the central (CNS) and the peripheral nervous systems. Activation of GLP-1R signaling by GLP-1RAs improves glucose homeostasis by enhancing glucose-stimulated insulin secretion, delaying gastric emptying and decreasing plasma glucagon levels, and reduces body weight by activating anorexigenic pathways in the brain. Due to the glucose-dependence of beta-cell activation, GLP-1RAs are not associated with increased risk of hypoglycaemia. While the broad metabolic benefits of GLP-1RAs have established this class in the T2DM treatment paradigm, many patients do not reach their HbA1c/glycaemic targets and weight loss achieved with these agents, thus, requiring a higher dose, which also increases GI adverse events, and remains well below what can be attained with bariatric surgery, the most potent clinical intervention for obesity. Thus, there are significant opportunities to improve upon the existing GLP-1RA class.

One emerging approach is to combine foundational GLP-1RA therapy with pharmacological strategies targeting additional pathways implicated in nutrient and energy metabolism, such as the glucose-dependent insulinotropic polypeptide (GIP) pathway. GIP is an incretin that is secreted from K cells in the upper small intestine, duodenum, in response to food. Postprandial GIP levels are approximately 4-fold higher compared to GLP-1 under normal physiological conditions. GIP is responsible for the majority of the insulinotropic incretin effect in man, and has important additional functions that are distinct from GLP-1. Unlike GLP-1, GIP is both glucagonotropic and insulinotropic in a glycaemic-dependent manner, dose-dependently stimulating glucagon secretion under hypoglycaemic conditions and insulin under hyperglycaemic conditions, glucagon released does facilitate insulin secretion. Although both GIP-receptor (GIPR) and GLP-1R are present in beta-cells, GIPR expression is distributed differently in extra-pancreatic tissues as GIPR is abundant in adipose tissue and is found in many non-overlapping areas of the CNS. GIP is implicated in adipose tissue carbohydrate and lipid metabolism by its actions to regulate glucose uptake, lipolysis and lipoprotein lipase activity. The findings suggest that pharmacological activation of GIPR may have a therapeutic benefit on peripheral energy metabolism. Recently, unimolecular, multi-functional peptides that combine GLP-1RA activity with GIP activity have been suggested as new therapeutic agents for glycaemic and weight control.

U.S. Pat. No. 9,474,780 discloses dual GLP-1 and GIP receptor agonists including tirzepatide.

(SEQ ID NO: 13)

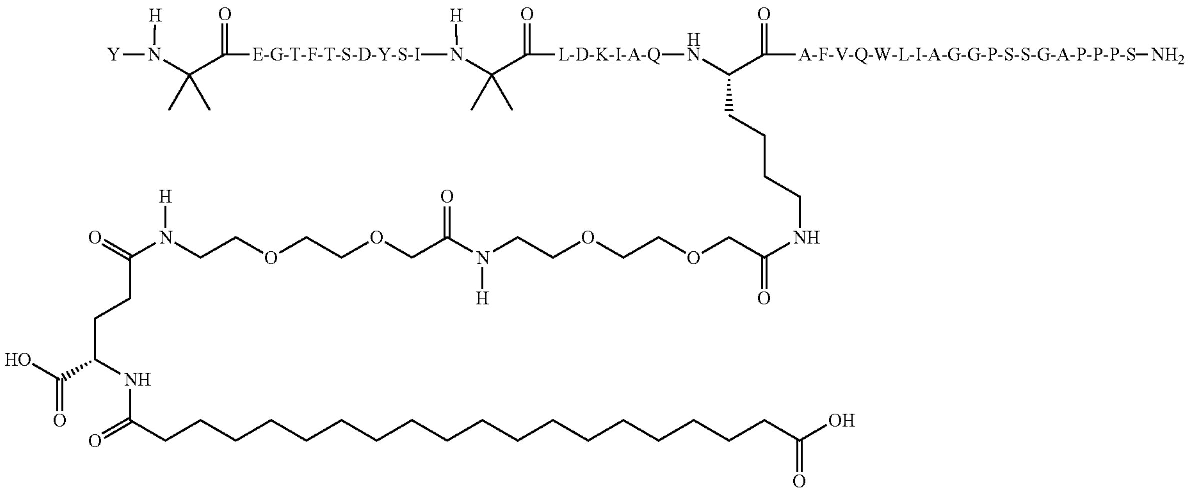

Tirzepatide

Tirzepatide is under Phase-III clinical studies for T2DM and obesity.

WIPO publication numbers WO2017/74714A1, WO2020/23386A1, WO2020/023388A1, WO2015/067715A2, WO2016/111971A1 and WO2013/164483A1 disclose GLP-1 R and GIP R dual agonist compounds.

SUMMARY OF THE INVENTION

The present invention provides a polypeptide or a pharmaceutically acceptable salt thereof, comprising an amino acid sequence:

(Seq. ID 1)
Y-X1-E-G-T-F-T-S-D-Y-S-I-X2-L-Xaa15-K-I-A-Xaa19-
X3-Xaa21-F-V-Xaa24-W-L-X4-A-G-G-P-S-S-G-A-P-P-P-
S-X5-X6-X7-X8-X9-X10-X11 wherein X1 is Aib, (L)-norvaline or (D)-norvaline;

X2 is selected from Aib, Leu, (D)-Leu, Val, (D)-Val, Ile, (D)-Ile, and L or D isomer of an amino acid of Formula

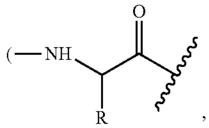
, wherein "" represents the point of attachment to Leu and R is selected from $C_{2-5}$alkyl, $C_{3-7}$cycloalkyl, $C_{3-7}$cyclolalkyl-$C_{1-3}$alkyl-, $C_{3-5}$alkenyl, $C_{3-5}$alkynyl, $C_{5-7}$cycloalkenyl-$CH_2$—, and $C_{1-3}$haloalkyl-; or R along with the carbon to which it is attached, forms a $C_{3-6}$cycloalkyl ring:

X3 is Gln or Lys; wherein, when X3 is Lys, the side chain amino (ε amino) group of Lys is acylated with a moiety:

{—U—W—Y—Z wherein U is —C(O)—$CH_2$—O—$(CH_2)_2$—O—$(CH_2)_2$—NH—} wherein} is point of attachment with group W;

W is selected from a group consisting of —C(O)—NH—$(CH_2)_p$—NH—], —C(O)—$C(CH_3)_2$—NH—] and —C(O)—$CH_2$—O—$(CH_2)_2$—O—$(CH_2)_2$—NH—], wherein p is 3 or 4 and wherein] is point of attachment with group Y;

Y is —C(O)—$(CH_2)_2$—CH(COOH)NH— and — is point of attachment with the group Z;

Z is —C(O)—$(CH_2)_n$—COOH or —C(O)—$(CH_2)_n$—$CH_3$ wherein n is an integer from 14 to 20;

X4 is Leu, Ile or Glu;

X5 is absent, Arg or Lys; wherein when X5 is Lys, the side chain amino (ε amino) group of Lys is acylated with a moiety:

{—U′—W′—Y′—Z′ wherein U' is —C(O)—$CH_2$—O—$(CH_2)_2$—O—$(CH_2)_2$—NH—} wherein} is point of attachment with group W';

W' is selected from a group consisting of —C(O)—NH—$(CH_2)_q$—NH—], —C(O)—$C(CH_3)_2$—NH—] and —C(O)—$CH_2$—O—$(CH_2)_2$—O—$(CH_2)_2$—NH—], wherein q is 3 or 4 and wherein] is point of attachment with group Y';

Y' is —C(O)—$(CH_2)_2$—CH(COOH)NH— and — is point of attachment with the group Z';

Z' is —C(O)—$(CH_2)_n$—COOH or —C(O)—$(CH_2)_m$—$CH_3$ wherein m is an integer from 14 to 20;

X6 is absent or Lys;

X7 is absent or Lys;

X8 is absent or Lys;

X9 is absent or Lys;

X10 is absent or Lys;

X11 is absent or Lys;

Xaa15 is Asp or Glu;

Xaa19 is Gln or Ala;

Xaa21 is Ala or Glu;

Xaa24 is Gln or Asn;

wherein the acid group of the C terminal amino acid is a free carboxylic acid group or is amidated as a C-terminal primary amide and at least one of X3 and X5 is Lys; and with the proviso that when X1 is Aib, X2 is not Aib.

Abbreviations

Aib: 2-Aminoisobutyric acid
DIPEA: N,N'-Di-isopropylethylamine
HOBt: 1-Hydroxy benztriazole
DIPC: N,N'-Di-isopropylcarbodiimide
THF: Tetrahydrofuran
DCM: Dichloromethane

DETAILED DESCRIPTION OF THE INVENTION

"Pharmaceutically acceptable salt" according to the invention include acid addition salts formed with either organic or inorganic acids. Suitable pharmaceutically acceptable salts of the compounds of the invention include acid addition salts which may be salts of inorganic acids such as hydrochloric acid, hydrobromic acid, phosphoric acid, and the like or of organic acids such as, for example, acetic acid, benzenesulfonic acid, methanesulfonic acid, benzoic acid, citric acid, lactic acid, fumaric acid, succinic acid, adipic acid, pimelic acid, suberic acid, azelaic acid, malic acid, tartaric acid, amino acids such as glutamic acid or aspartic acid, and the like. The pharmaceutically acceptable acid addition salt of the compounds of the present invention includes salts formed with the addition of one or more equivalents of acids, for example, monohydrochloride, dihydrochloride salts, etc. Salts can be prepared by any process under the purview of an ordinary person skilled in the art. (See Berge et al., J. Pharm. Sci. 1977, 66, 1-19; and Handbook of Pharmaceutical Salts, Properties, and Use; Stahl and Wermuth, Ed.: Wiley-VCH and VHCA: Zurich, Switzerland, 2002).

The term "alkyl" as used herein refers to a saturated hydrocarbon chain radical that includes solely carbon and hydrogen atoms in the backbone, either linear or branched, having from 1 to 6 carbon atoms, both inclusive unless defined otherwise and which is attached to the rest of the molecule by a single bond. Suitable non-limiting examples of alkyl groups include, e.g., methyl, ethyl, n-propyl, 1-methylethyl (isopropyl), n-pentyl, n-hexyl, etc.

The term "haloalkyl" as used herein refers to any "alkyl" having one or more hydrogen atom(s) replaced by a halogen atom, wherein halogen atom may be selected from fluorine, chlorine, bromine or iodine.

The numerical in phrases like "$C_{2-5}$", refers to the number of carbon atoms in the chain. For example, the phrase "$C_{2-5}$ alkyl" refers to an alkyl chain having 2 to 5 carbon atoms.

The term "alkenyl" as used herein refers to a hydrocarbon chain containing at least one carbon-carbon double bond, and may have (E) or (Z) configuration. An alkenyl group may contain 2 to 8 carbon atoms unless specified otherwise. Unless set forth or recited to the contrary, all alkenyl groups described herein may form part of a straight or branched chain. Suitable non-limiting examples of alkenyl groups include, e.g., ethylene, 2-propenyl (allyl), 2-methyl-2-propenyl and 2-butenyl.

The term "alkynyl" refers to a hydrocarbon chain having at least one carbon-carbon triple bond. An alkynyl group may contain 2 to 8 carbon atoms unless specified otherwise. Unless set forth or recited to the contrary all alkynyl groups described or claimed herein may form part of a straight or branched chains. The non-limiting examples of alkynyl groups include 2-propynyl, 3-butynyl and propargyl.

The term "cycloalkyl" as used herein refers to a non-aromatic monocyclic ring system of 3 to 7 carbon atoms unless specified otherwise. Cycloalkyl ring include, but are not limited to, cyclopropyl, cyclobutyl, cyclopentyl, cyclohexyl and cycloheptyl.

The term "cycloalkenyl" refers to a non-aromatic monocyclic 5 to 7 membered cycloalkyl ring system, with at least one carbon-carbon double bond. The non-limiting examples of cycloalkenylmethyl group includes cyclopentenylmethyl and cyclohexenylmethyl.

The term "effective amount or amount effective" as used herein refers to an amount of the compound which is sufficient, upon single or multiple dose administration(s) to a subject, in curing, alleviating, relieving or partially addressing the clinical manifestation of given disease or state and its complications beyond that expected in the absence of such treatment. Thus, the result can be reduction and/or alleviation of the signs, symptoms, or causes of a disease, or any other desired alteration of a biological system. It is understood that "a therapeutically effective amount" can vary from subject to subject depending on age, weight, general condition of the subject, the condition being treated, the severity of the condition being treated, and the judgment of the prescribing physician.

The amino acid "norvaline" as used herein can be represented by structure

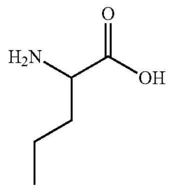

and can also be defined by the chemical name as "2-aminopentanoic acid". The term (L)-norvaline and (D)-norvaline refers to "L" and "D" isomer of norvaline, respectively.

The amino acid "norleucine" as used herein can be represented by structure

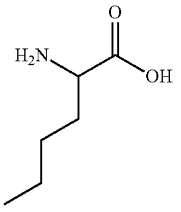

and can also be defined by the chemical name as "2-Aminohexanoic acid". The term (L)-norleucine and (D)-norleucine refers to "L" and "D" isomer of norleucine, respectively.

The amino acid "homoalanine" as used herein can be represented by structure

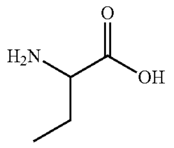

and can also be defined by the chemical name as "2-aminobutyric acid". The term (L)-homoalanine and (D)-homoalanine refers to "L" and "D" isomer of homoalanine, respectively.

The present invention provides stable long acting GLP-1/GIP agonist polypeptides which may be useful for treating type 2 diabetes mellitus (T2D), diabetes with obesity, obesity and hyperlipidemia. The polypeptides of present invention are long acting which may not require frequent administration to a patient in need thereof.

Accordingly, in one aspect, the present invention provides a polypeptide or a pharmaceutically acceptable salt thereof, comprising an amino acid sequence:

```
                                        (Seq. ID 1)
Y-X1-E-G-T-F-T-S-D-Y-S-I-X2-L-Xaa15-K-I-A-Xaa19-

X3-Xaa21-F-V-Xaa24-W-L-X4-A-G-G-P-S-S-G-A-P-P-P-

S-X5-X6-X7-X8-X9-X10-X11
```

wherein X1 is Aib, (L)-norvaline or (D)-norvaline;

X2 is selected from Aib, Leu, (D)-Leu, Val, (D)-Val, Ile, (D)-Ile, and L or D isomer of an amino acid of Formula

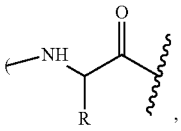, wherein " " represents the point of attachment to Leu, R is selected from $C_{2-5}$alkyl, $C_{3-7}$cycloalkyl, $C_{3-7}$cyclolalkyl-$C_{1-3}$alkyl-, $C_{3-5}$alkenyl, $C_{3-5}$alkynyl, $C_{5-7}$cycloalkenyl-$CH_2$—, and $C_{1-3}$haloalkyl; or R along with the carbon to which it is attached to, forms $C_{3-6}$cycloalkyl ring:

X3 is Gln or Lys; wherein, when X3 is Lys, the side chain amino (ε amino) group of Lys is acylated with a moiety:

{—U—W—Y—Z wherein U is —C(O)—$CH_2$—O—$(CH_2)_2$—O—$(CH_2)_2$—NH—} wherein} is point of attachment with group W;

W is selected from a group consisting of —C(O)—NH—$(CH_2)_p$—NH—], —C(O)—$C(CH_3)_2$—NH—] and —C(O)—$CH_2$—O—$(CH_2)_2$—O—$(CH_2)_2$—NH—], wherein p is 3 or 4 and wherein] is point of attachment with group Y;

Y is —C(O)—$(CH_2)_2$—CH(COOH)NH— and — is point of attachment with the group Z;

Z is —C(O)—$(CH_2)_n$—COOH or —C(O)—$(CH_2)_n$—$CH_3$ wherein n is an integer from 14 to 20;

X4 is Leu, Ile or Glu;

X5 is absent, Arg or Lys; wherein when X5 is Lys, the side chain amino (ε amino) group of Lys is acylated with a moiety:

{—U'—W'—Y'—Z' wherein U' is —C(O)—$CH_2$—O—$(CH_2)_2$—O—$(CH_2)_2$—NH—} wherein} is point of attachment with group W';

W' is selected from a group consisting of —C(O)—NH—$(CH_2)_q$NH—], —C(O)—$C(CH_3)_2$—NH—] and —C(O)—$CH_2$—O—$(CH_2)_2$—O—$(CH_2)_2$—NH—], wherein q is 3 or 4 and wherein] is point of attachment with group Y';

Y' is —C(O)—$(CH_2)_2$—CH(COOH)NH— and — is point of attachment with the group Z';

Z' is —C(O)—$(CH_2)_m$—COOH or —C(O)—$(CH_2)_m$—$CH_3$ wherein m is an integer from 14 to 20;

X6 is absent or Lys;

X7 is absent or Lys;

X8 is absent or Lys;

X9 is absent or Lys;

X10 is absent or Lys;

X11 is absent or Lys;

Xaa15 is Asp or Glu;

Xaa19 is Gln or Ala;

Xaa21 is Ala or Glu;

Xaa24 is Gln or Asn;

wherein the acid group of the C terminal amino acid is a free carboxylic acid group or is amidated as a C-terminal primary amide and at least one of X3 and X5 is Lys; and with the proviso that when X1 is Aib, X2 is not Aib.

In one embodiment of the present invention, X1 is Aib.

In another embodiment of the present invention, X2 is Aib.

In another embodiment of present invention, X4 is Ile.

In another embodiment of the present invention, X1 is (L)-norvaline.

In another embodiment of the present invention, X2 is Leu.

In another embodiment of the present invention, X2 is Ile.

In another embodiment of the present invention, X2 is selected from a L or D isomer of an amino acid of the Formula

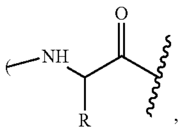
, wherein "" represents the point of attachment to Leu, and R is selected from $C_{2-5}$alkyl, $C_{3-7}$cycloalkyl, $C_{3-7}$cyclolalkyl-$C_{1-3}$alkyl-, $C_{3-5}$alkenyl, $C_{3-5}$alkynyl, $C_{5-7}$cycloalkenyl-$CH_2$—, and $C_{1-3}$haloalkyl; or R along with the carbon to which it is attached to, forms $C_{3-6}$cycloalkyl ring.

In another embodiment of the present invention, X2 is an amino acid of the Formula

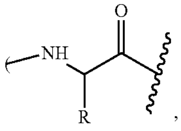
, which is present in "L" configuration.

In another embodiment, of the present invention, X2 is an amino acid of the Formula

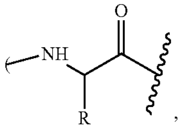
, which is present in "D" configuration.

In another embodiment of the present invention, X2 is an amino acid of the Formula

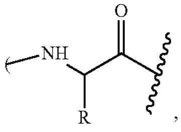
, wherein, R is $C_{2-5}$alkyl. In another embodiment, R is selected from ethyl, n-propyl, isopropyl and n-butyl.

In yet another embodiment of the present invention, X2 is an amino acid of the Formula

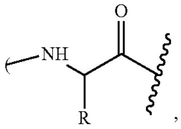
, wherein, R is n-propyl, thus forming X2 as norvaline. In another embodiment, X2 is (L)-norvaline. In another embodiment, X2 is (D)-norvaline.

In yet another embodiment of the present invention, X2 is an amino acid of the Formula

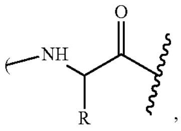
, wherein, R is n-butyl, thus forming X2 as norleucine. In another embodiment, X2 is (L)-norleucine. In another embodiment, X2 is (D)-norleucine.

In yet another embodiment of the present invention, X2 is an amino acid of the Formula

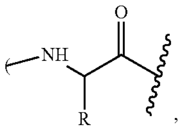
, wherein, R is ethyl, thus forming X2 as homoalanine. In another embodiment, X2 is (L)-homoalanine. In another embodiment, X2 is (D)-homoalanine.

In another embodiment of the present invention, X2 is an amino acid of the Formula

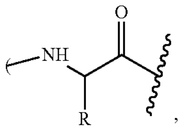
, wherein, R is $C_{3-7}$cyclolalkyl-$C_{1-3}$alkyl-. In another embodiment, R is selected from cyclopropylmethyl-, cyclopentylmethyl- and cyclohexylmethyl-.

In another embodiment of the present invention, X2 is an amino acid of the Formula

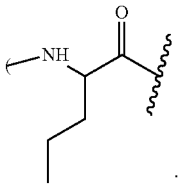 [SMILES: *C(=O)C(CCC)NC]
.

In another embodiment of the present invention, X2 is an amino acid of the Formula

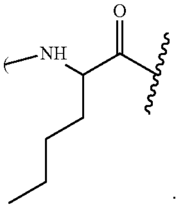 [SMILES: *C(=O)C(CCCC)NC]
.

In another embodiment of the present invention, X2 is an amino acid of the Formula

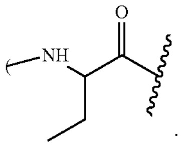 [SMILES: *C(=O)C(CC)NC]
.

In another embodiment of the present invention, X1 is Aib and X2 is L-isomer of an amino acid of the Formula

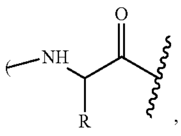
, wherein, R is n-propyl, i.e., X2 is (L)-norvaline.

In another embodiment of the present invention, X1 is Aib and X2 is L-isomer of an amino acid of the Formula

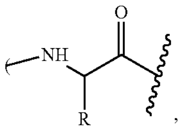
, wherein, R is ethyl, i.e., X2 is (L)-homoalanine.

In another embodiment of the present invention, X1 is Aib and X2 is L-isomer of an amino acid of the Formula

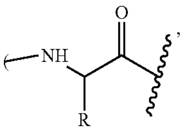

wherein, R is n-butyl, i.e., X2 is (L)-norleucine.

In another embodiment of the present invention, X1 is Aib and X2 is Leu.

In another embodiment of the present invention, X1 is Aib and X2 is Ile.

In another embodiment of the present invention, X1 is (L)-norvaline and X2 is Aib.

In another embodiment of the present invention, wherein X1 is (L)-norvaline and X2 is L-isomer of an amino acid of the Formula

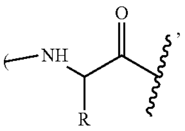

wherein, R is n-propyl, i.e., X2 is (L)-norvaline.

In one embodiment of the present invention, X1 is Aib or (L)-norvaline; and X2 is Aib, Leu, Ile or L isomer of an amino acid of the Formula

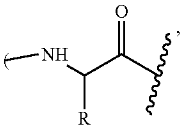

wherein, R is n-propyl and X1 and X2 are not both Aib.

In one embodiment of the present invention, X1 is Aib or (L)-norvaline; and X2 is Aib, Leu, Ile or L isomer of an amino acid of the Formula

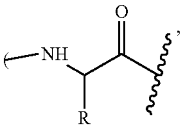

wherein, R is n-butyl and X1 and X2 are not both Aib.

In one embodiment of the present invention, X1 is Aib or (L)-norvaline; and X2 is Aib, Leu, Ile or L isomer of an amino acid of the Formula

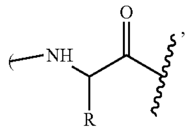

wherein, R is ethyl and X1 and X2 are not both Aib.

In one embodiment of the present invention, X1 is Aib or (L)-norvaline; X2 is Aib, Leu, Ile or L isomer of an amino acid of the Formula

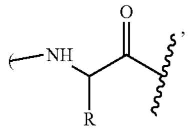

wherein, R is n-propyl; X4 is Ile; and X1 and X2 are not both Aib.

In one embodiment of the present invention, X1 is Aib or (L)-norvaline: X2 is Aib, Leu, Ile or L isomer of an amino acid of the Formula

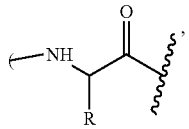

wherein, R is n-propyl; X5 is Arg and X1 and X2 are not both Aib.

In one embodiment of the present invention, X3 is Lys, wherein the side chain amino (ε amino) group of Lys is acylated with a moiety:

{—U—W—Y—Z

In another embodiment of present invention, W is —C(O)—C($CH_3$)$_2$—NH—].

In another embodiment of the present invention, W is —C(O)—NH—($CH_2$)$_p$—NH—], wherein p is 3 or 4.

In another embodiment of the present invention, W is —C(O)—$CH_2$—O—($CH_2$)$_2$—O—($CH_2$)$_2$—NH—].

In another embodiment of the present invention, Z is —C(O)—($CH_2$)$_n$—COOH and n is 16, 17, 18, 19 or 20. In a preferred embodiment n is 16, 18 or 20. In yet another preferred embodiment n 18 or 20.

In another preferred embodiment of the present invention, Z is —C(O)—($CH_2$)$_n$—COOH and n is 16 or 18. In yet another preferred embodiment n is 18.

In another embodiment of the present invention, W is —C(O)—C($CH_3$)$_2$—NH—] and Z is —C(O)—($CH_2$)$_n$—COOH, wherein n is 18.

In another embodiment of the present invention, W is —C(O)—C($CH_3$)$_2$—NH—] and Z is —C(O)—($CH_2$)$_n$—COOH, wherein n is 16.

In another embodiment of the present invention, W is —C(O)—$CH_2$—O—($CH_2$)$_2$—O—($CH_2$)$_2$—NH—] and Z is —C(O)—($CH_2$)$_n$—COOH, wherein n is 16.

In another embodiment of the present invention, W is —C(O)—$CH_2$—O—($CH_2$)$_2$—O—($CH_2$)$_2$—NH—] and Z is —C(O)—($CH_2$)$_n$—COOH, wherein n is 18.

In one embodiment of the present invention, X3 is Gln; and X5 is Lys, wherein the side chain amino (ε amino) group of Lys is acylated with a moiety:

{—U'—W'—Y'—Z',

In one embodiment of the present invention, X1 is Aib or (L)-norvaline: X2 is Aib, Leu, Ile or L isomer of an amino acid of the Formula

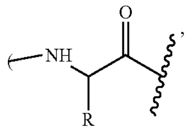

wherein, R is n-propyl; X3 is Gln; and X5 is Lys; and X1 and X2 are not both Aib: wherein the side chain amino (ε amino) group of Lys is acylated with a moiety:

{—U'—W'—Y'—Z',

In another embodiment of present invention, W' is —C(O)—C($CH_3$)$_2$—NH—].

In another embodiment of the present invention, W' is —C(O)—NH—($CH_2$)$_q$NH—], wherein q is 3 or 4.

In another embodiment of the present invention, W' is —C(O)—$CH_2$—O—($CH_2$)$_2$—O—($CH_2$)$_2$—NH—].

In another embodiment of the present invention, Z' is —C(O)—($CH_2$)$_m$—COOH and m is 16, 17, 18, 19 or 20. In a preferred embodiment, m is 16, 18 or 20. In yet another preferred embodiment m is 18 or 20.

In another preferred embodiment of the present invention, Z' is —C(O)—($CH_2$)$_m$—COOH and m is 16 or 18. In yet another preferred embodiment m is 18.

In another embodiment of the present invention, W' is —C(O)—C($CH_3$)$_2$—NH—] and Z' is —C(O)—($CH_2$)$_m$—COOH, wherein m is 18.

In another embodiment of the present invention, W' is —C(O)—C($CH_3$)$_2$—NH—] and Z' is —C(O)—($CH_2$)$_m$—COOH, wherein m is 16.

In another embodiment of the present invention, W' is —C(O)—$CH_2$—O—($CH_2$)$_2$—O—($CH_2$)$_2$—NH—] and Z' is —C(O)—($CH_2$)$_m$—COOH, wherein m is 16.

In another embodiment of the present invention, W' is —C(O)—$CH_2$—O—($CH_2$)$_2$—O—($CH_2$)$_2$—NH—] and Z' is —C(O)—($CH_2$)$_m$—COOH, wherein m is 18.

In one embodiment of the present invention, X1 is Aib; X2 is L isomer of an amino acid of the Formula

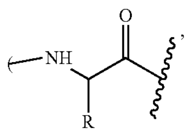

wherein, R is n-propyl; Xaa15 is Glu; Xaa19 is Ala; X3 is Gln; Xaa21 is Glu; Xaa24 is Asn; X4 is Leu; and X5 is Lys, wherein the side chain amino (ε amino) group of Lys is acylated with a moiety:

{—U'—W'—Y'—Z' wherein W' is —C(O)—C($CH_3$)$_2$—NH—]; and
Z' is —C(O)—($CH_2$)$_m$—COOH wherein m is 18.

In another embodiment of the present invention, the C terminal amino acid is amidated as a C-terminal primary amide.

In another embodiment of the present invention, X5, X6, X7, X8, X9, X10 and X11 are absent.

In another aspect, the present invention provides a polypeptide or a pharmaceutically acceptable salt thereof, comprising an amino acid sequence:

```
                                          (Seq. ID 2)
Y-Aib-E-G-T-F-T-S-D-Y-S-I-X2-L-D-K-I-A-Q-X3-A-F-V-

Q-W-L-X4-A-G-G-P-S-S-G-A-P-P-P-S-X5-X6-X7-X8-X9-

X10-X11
```

wherein X2 is Leu, Ile, (L)-norvaline, (L)-homoalanine or (L)-norleucine;
X4 is Ile;
X5 is absent or Arg;
X6 is absent or Lys;
X7 is absent or Lys;
X8 is absent or Lys;
X9 is absent or Lys;
X10 is absent or Lys;
X11 is absent or Lys;
X3 is Lys wherein the side chain amino (ε amino) group of Lys is acylated with a moiety:

{—U—W—Y—Z wherein U is —C(O)—$CH_2$—O—$(CH_2)_2$—O—$(CH_2)_2$—NH—} wherein} is point of attachment with group W;
W is selected from a group consisting of —C(O)—NH—$(CH_2)_p$—NH—], —C(O)—$C(CH_3)_2$—NH—] and —C(O)—$CH_2$—O—$(CH_2)_2$—O—$(CH_2)_2$—NH—], wherein p is 3 or 4 and wherein] is point of attachment with group Y;
Y is —C(O)—$(CH_2)_2$—CH(COOH)NH— and — is point of attachment with the group Z;
Z is —C(O)—$(CH_2)_n$—COOH or —C(O)—$(CH_2)_n$—$CH_3$ wherein n is an integer from 14 to 20; and
wherein the acid group of the C terminal amino acid is a free carboxylic acid group or is amidated as a C-terminal primary amide.

In one embodiment of the present invention, X2 is (L)-norvaline.

In one embodiment of the present invention, X2 is (L)-homoalanine.

In one embodiment of the present invention, X2 is (L)-norleucine.

In another embodiment of the present invention, X2 is Leu.

In another embodiment of the present invention, X2 is Ile.

In another embodiment of the present invention, X2 is (L)-norvaline and X5 is Arg.

In another embodiment of present invention, W is —C(O)—$C(CH_3)_2$—NH—].

In another embodiment of the present invention, W is —C(O)—NH—$(CH_2)_3)_2$—NH—].

In another embodiment of the present invention, W is —C(O)—$CH_2$—O—$(CH_2)_2$—O—$(CH_2)_2$—NH—].

In another embodiment of the present invention, Z is —C(O)—$(CH_2)_n$—COOH and n is 16, 17, 18, 19 or 20. In a preferred embodiment n is 16, 18 or 20. In yet another preferred embodiment n is 18 or 20.

In another preferred embodiment of the present invention, Z is —C(O)—$(CH_2)_n$—COOH and n is 16 or 18. In yet another preferred embodiment n is 18.

In another embodiment of the present invention, W is —C(O)—$C(CH_3)_2$—NH—] and Z is —C(O)—$(CH_2)_n$—COOH, wherein n is 18.

In another embodiment of the present invention, W is —C(O)—$C(CH_3)_2$—NH—] and Z is —C(O)—$(CH_2)_n$—COOH, wherein n is 16.

In another embodiment of the present invention, W is —C(O)—$CH_2$—O—$(CH_2)_2$—O—$(CH_2)_2$—NH—] and Z is —C(O)—$(CH_2)_n$—COOH, wherein n is 16.

In another embodiment of the present invention, W is —C(O)—$CH_2$—O—$(CH_2)_2$—O—$(CH_2)_2$—NH—] and Z is —C(O)—$(CH_2)_n$—COOH, wherein n is 18.

In another embodiment of the present invention, the C terminal amino acid is amidated as a C-terminal primary amide.

In another embodiment of the present invention, X5, X6, X7, X8, X9, X10 and X11 are absent.

In a preferred embodiment X2 is (L)-norvaline, X4 is Ile; X5, X6, X7, X8, X9, X10 and X11 are absent; W is —C(O)—$C(CH_3)_2$—NH—]; and Z is —C(O)—$(CH_2)_n$—COOH, wherein n is 18.

In another aspect, the present invention provides a polypeptide or a pharmaceutically acceptable salt thereof, comprising an amino acid sequence:

```
                                          (Seq. ID 3)
Y-X1-E-G-T-F-T-S-D-Y-S-I-X2-L-D-K-I-A-Q-X3-A-F-V-

Q-W-L-X4-A-G-G-P-S-S-G-A-P-P-P-S
```

wherein X1 is Aib or (L)-norvaline; X2 is Aib, Leu, Ile, (L)-norvaline, (L)-homoalanine or (L)-norleucine;
X4 is Ile;
X3 is Lys wherein the side chain amino (ε amino) group of Lys is acylated with a moiety:

{—U—W—Y—Z wherein U is —C(O)—$CH_2$—O—$(CH_2)_2$—O—$(CH_2)_2$—NH—} wherein} is point of attachment with group W;
W is selected from a group consisting of —C(O)—NH—$(CH_2)_p$—NH—], —C(O)—$C(CH_3)_2$—NH—] and —C(O)—$CH_2$—O—$(CH_2)_2$—O—$(CH_2)_2$—NH—], wherein p is 3 or 4 and wherein] is point of attachment with group Y;
Y is —C(O)—$(CH_2)_2$—CH(COOH)NH— and — is point of attachment with the group Z;
Z is —C(O)—$(CH_2)_n$—COOH or —C(O)—$(CH_2)_n$—$CH_3$ wherein n is an integer from 14 to 20;
and wherein the acid group of the C terminal amino acid is a free carboxylic acid group or is amidated as a C-terminal primary amide,
with a proviso that when X1 is Aib, X2 is not Aib.

In one embodiment of the present invention, X1 is Aib.

In another embodiment of the present invention, X1 is (L)-norvaline.

In another embodiment of the present invention, X2 is Aib.

In another embodiment of the present invention, X2 is (L)-norvaline.

In another embodiment of the present invention, X2 is (L)-norleucine.

In another embodiment of the present invention, X2 is (L)-homoalanine.

In another embodiment of the present invention, X2 is Leu.

In another embodiment of the present invention, X2 is Ile.

In another embodiment of the present invention, X1 is Aib and X2 is (L)-norvaline.

In another embodiment of the present invention, X1 is Aib and X2 is (L)-norleucine.

In another embodiment of the present invention, X1 is Aib and X2 is (L)-homoalanine.

In another embodiment of the present invention, X1 is (L)-norvaline and X2 is Aib.

In another embodiment of the present invention, X1 is Aib and X2 is Leu.

In another embodiment of the present invention, X1 is Aib and X2 is Ile.

In another embodiment of the present invention, X1 is (L)-norvaline and X2 is (L)-norvaline.

In another embodiment of present invention, W is $—C(O)—C(CH_3)_2—NH—]$.

In another embodiment of the present invention, W is $—C(O)—NH—(CH_2)_{3-4}—NH—]$.

In another embodiment of the present invention, W is $—C(O)—CH_2—O—(CH_2)_2—O—(CH_2)_2—NH—]$.

In another embodiment of the present invention, Z is $—C(O)—(CH_2)_n—COOH$ and n is 16, 17, 18, 19 or 20. In a preferred embodiment n is 16, 18 or 20. In yet another preferred embodiment n is 18 or 20.

In another preferred embodiment of the present invention, Z is $—C(O)—(CH_2)_n—COOH$ and n is 16 or 18. In yet another preferred embodiment n is 18.

In another embodiment of the present invention, W is $—C(O)—C(CH_3)_2—NH—]$ and Z is $—C(O)—(CH_2)_n—COOH$, wherein n is 18.

In another embodiment of the present invention, W is $—C(O)—C(CH_3)_2—NH—]$ and Z is $—C(O)—(CH_2)_n—COOH$, wherein n is 16.

In another embodiment of the present invention, W is $—C(O)—CH_2—O—(CH_2)_2—O—(CH_2)_2—NH—]$ and Z is $—C(O)—(CH_2)_n—COOH$, wherein n is 16.

In another embodiment of the present invention, W is $—C(O)—CH_2—O—(CH_2)_2—O—(CH_2)_2—NH—]$ and Z is $—C(O)—(CH_2)_n—COOH$, wherein n is 18.

In another embodiment of the present invention, X1 is Aib; X2 is (L)-norvaline; and X3 is Lys wherein the side chain amino (ε amino) group of Lys is acylated with a moiety:

{—U—W—Y—Z wherein W is $—C(O)—C(CH_3)_2—NH—]$; Z is $—C(O)—(CH_2)_n—COOH$ and n is 18.

In another embodiment of the present invention, the C terminal amino acid is amidated as a C-terminal primary amide.

In another aspect, the present invention provides a polypeptide or pharmaceutically acceptable salt thereof comprising an amino acid sequence selected from the group consisting of:

i.)
(Seq ID: 04)
Tyr Aib Glu Gly Thr Phe Thr Ser Asp Tyr Ser Ile
L-norvaline Leu Asp Lys Ile Ala Gln Lys Ala Phe
Val Gln Trp Leu Ile Ala Gly Gly Pro Ser Ser Gly
Ala Pro Pro Pro Ser-$NH_2$ -continued ii.)
(Seq ID: 05)
Tyr L-norvaline Glu Gly Thr Phe Thr Ser Asp Tyr
Ser Ile Aib Leu Asp Lys Ile Ala Gln Lys Ala Phe
Val Gln Trp Leu Ile Ala Gly Gly Pro Ser Ser Gly
Ala Pro Pro Pro Ser-$NH_2$ iii.)
(Seq ID: 06)
Tyr Aib Glu Gly Thr Phe Thr Ser Asp Tyr Ser Ile
Leu Leu Asp Lys Ile Ala Gln Lys Ala Phe Val Gln
Trp Leu Ile Ala Gly Gly Pro Ser Ser Gly Ala Pro
Pro Pro Ser-$NH_2$ iv.)
(Seq ID: 07)
Tyr L-norvaline Glu Gly Thr Phe Thr Ser Asp Tyr
Ser Ile L-norvaline Leu Asp Lys Ile Ala Gln Lys
Ala Phe Val Gln Trp Leu Ile Ala Gly Gly Pro Ser
Ser Gly Ala Pro Pro Pro Ser-$NH_2$ v.)
(Seq ID: 08)
Tyr Aib Glu Gly Thr Phe Thr Ser Asp Tyr Ser Ile
L-norvaline Leu Glu Lys Ile Ala Ala Gln Glu Phe
Val Asn Trp Leu Leu Ala Gly Gly Pro Ser Ser Gly
Ala Pro Pro Pro Ser Lys-$NH_2$ vi.)
(Seq ID: 09)
Tyr Aib Glu Gly Thr Phe Thr Ser Asp Tyr Ser Ile
L-norvaline Leu Asp Lys Ile Ala Gln Lys Ala Phe
Val Gln Trp Leu Ile Ala Gly Gly Pro Ser Ser Gly
Ala Pro Pro Pro Ser Arg vii.)
(Seq ID: 10)
Tyr Aib Glu Gly Thr Phe Thr Ser Asp Tyr Ser Ile
L-homoalanine Leu Asp Lys Ile Ala Gln Lys Ala
Phe Val Gln Trp Leu Ile Ala Gly Gly Pro Ser Ser
Gly Ala Pro Pro Pro Ser-$NH_2$ viii.)
(Seq ID: 11)
Tyr Aib Glu Gly Thr Phe Thr Ser Asp Tyr Ser Ile
L-norleucine Leu Asp Lys Ile Ala Gln Lys Ala
Phe Val Gln Trp Leu Ile Ala Gly Gly Pro Ser Ser
Gly Ala Pro Pro Pro Ser-$NH_2$ ix.)
(Seq ID: 12)
Tyr Aib Glu Gly Thr Phe Thr Ser Asp Tyr Ser Ile
Ile Leu Asp Lys Ile Ala Gln Lys Ala Phe Val Gln
Trp Leu Ile Ala Gly Gly Pro Ser Ser Gly Ala Pro
Pro Pro Ser-$NH_2$ In another aspect, the present invention provides a polypeptide or pharmaceutically acceptable salt thereof, selected from the representative compounds as disclosed in the Table 1.

In the embodiments of the present invention, the groups U, W, Y and Z in the moiety

{—U—W—Y—Z or the groups U', W', Y' and Z' in the moiety

{—U'—W'—Y'—Z' have meaning as defined in this specification and should not be interpreted as or mixed with the single letter code of the amino acids;

In embodiments of the present invention, the group {—U—W—Y—Z and/or {—U'—W'—Y'—Z' is selected from the representative structures of Moiety A, B, C and D as disclosed in Table 2.

The polypeptide sequences mentioned in the specification are represented by the single letter code of the amino acids as approved by IUPAC.

Unless stated otherwise, the specification intends to cover both L and D isomers of the amino acids in the sequence. However, in preferred embodiments, all the amino acids are in "L" configuration unless indicated otherwise.

Table 1 and 2 provides some of the representative compounds of the present invention.

TABLE 1

Representative polypeptide compounds of present disclosure

| Compd No. | Structure | SEQ ID |
|---|---|---|
| 1 | 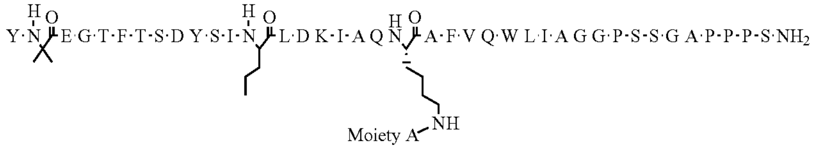 | 04 |
| 2 | 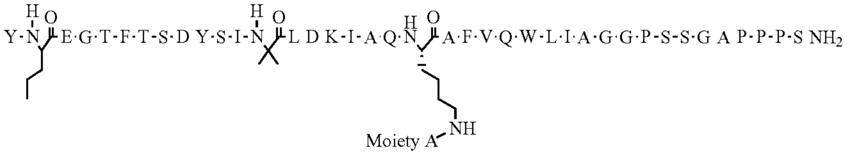 | 05 |
| 3 | 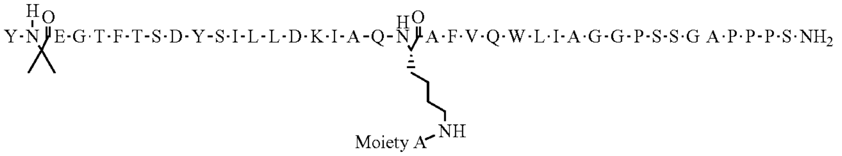 | 06 |
| 4 | 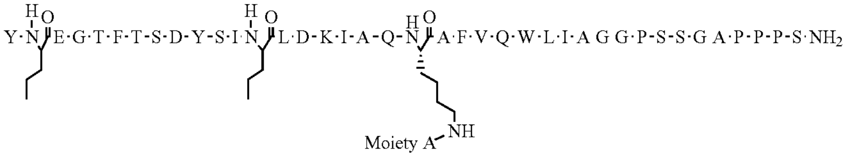 | 07 |
| 5 | 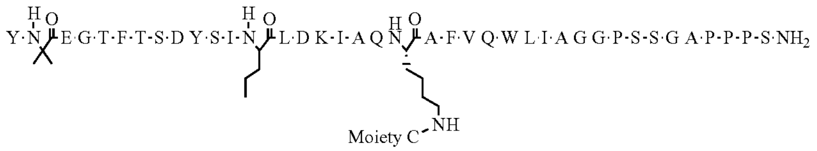 | 04 |
| 6 | 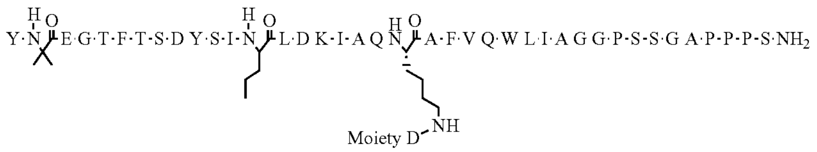 | 04 |

TABLE 1-continued
Representative polypeptide compounds of present disclosure
| Compd No. | Structure | SEQ ID |
|---|---|---|
| 7 | 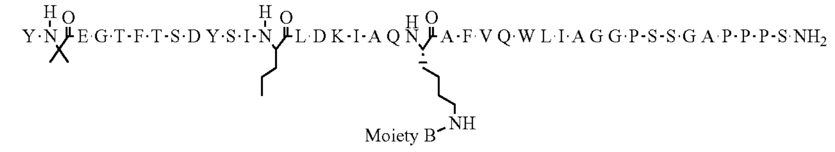 | 04 |
| 8 | 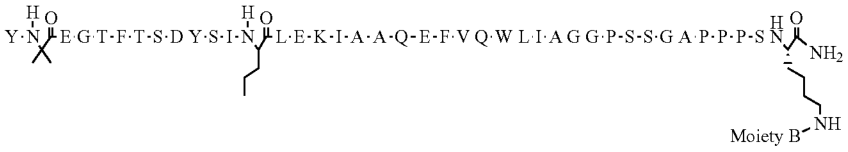 | 08 |
| 9 | 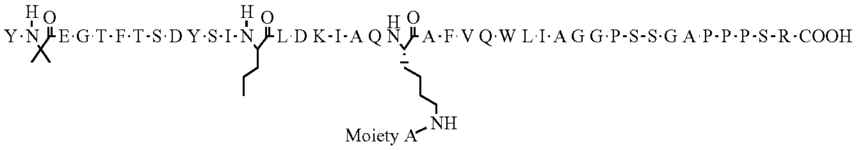 | 09 |
| 10 | 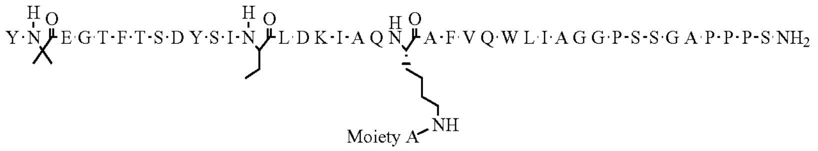 | 10 |
| 11 | 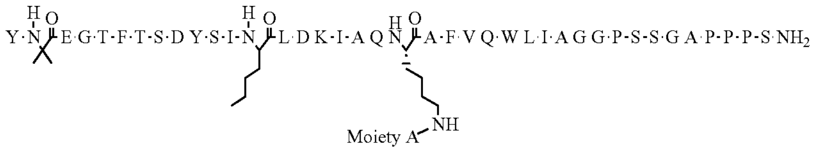 | 11 |
| 12 | 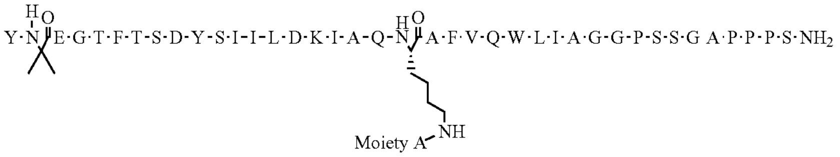 | 12 |
*Unless stated otherwise all the amino acids mentioned are in "L" configuration.

TABLE 2

| Structure of Moiety A, Moiety B, Moiety C and Moiety D | |
| --- | --- |
| Moiety A | 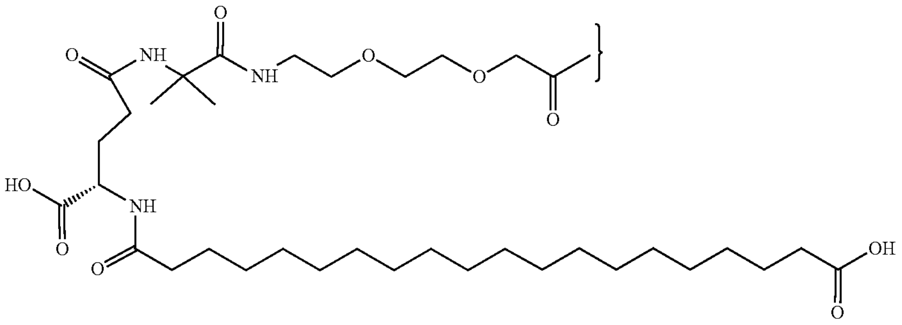 Moiety A |
| Moiety B | 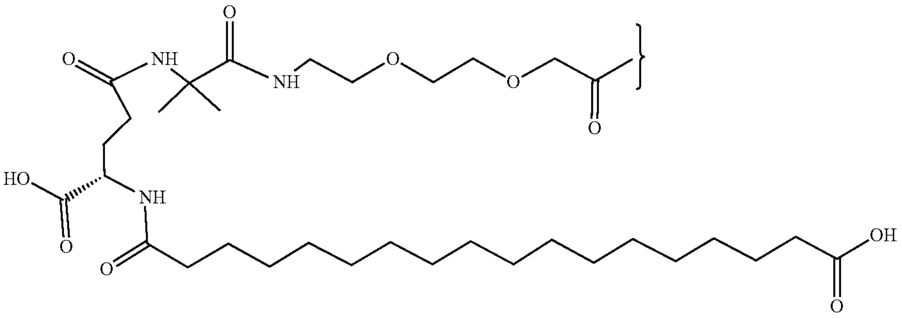 Moiety B |
| Moiety C | 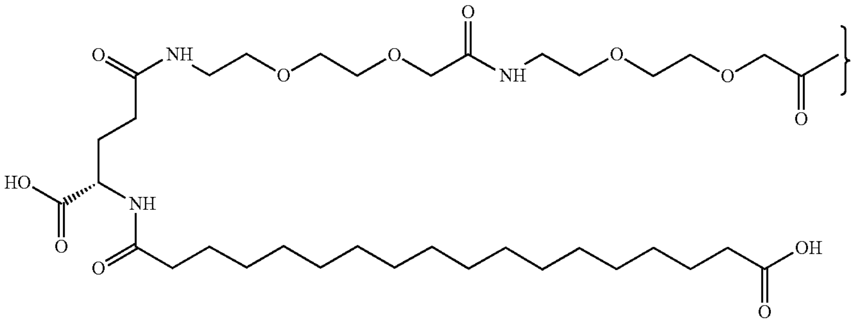 Moiety C |
| Moiety D | 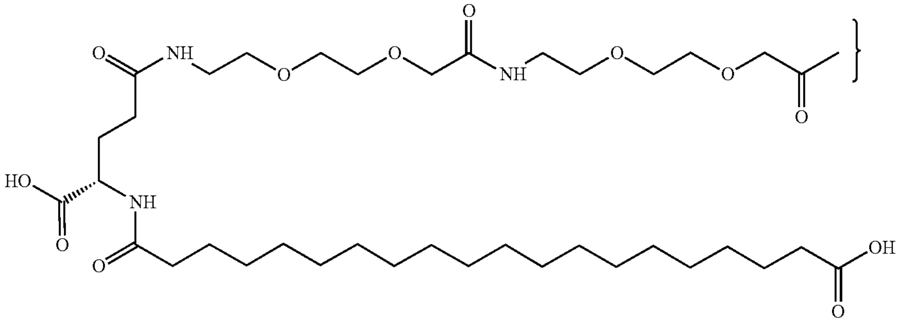 Moiety D |

In another aspect, the present invention provides a method of treating or preventing hyperglycemia, type 2 diabetes, impaired glucose tolerance, type 1 diabetes, obesity, hypertension, hyperlipidemia, syndrome X, dyslipidemia, cognitive disorders, atherosclerosis, myocardial infarction, coronary heart disease, stroke, inflammatory bowel syndrome, dyspepsia, alcoholism and gastric ulcers in a patient, comprising administering to a patient in need thereof, an effective amount of a polypeptide of the present invention or a pharmaceutically acceptable salt thereof.

In another aspect, the present invention provides a method of treatment of type 2 diabetes in a patient comprising administering to a patient in need of such treatment an effective amount of a compound of the present invention, or a pharmaceutically acceptable salt thereof.

In another aspect, the present invention provides a method of treatment of obesity in a patient comprising administering to a patient in need of such treatment an effective amount of a compound of the present invention, or a pharmaceutically acceptable salt thereof.

In another aspect, the present invention provides a method of treatment of hyperlipidemia in a patient comprising administering to a patient in need of such treatment an effective amount of a compound of the present invention, or a pharmaceutically acceptable salt thereof.

In an embodiment, the present invention provides a pharmaceutical composition comprising a polypeptide of the present invention or a pharmaceutically acceptable salt thereof with one or more of a pharmaceutically acceptable carrier, diluent, or excipient.

The compounds of the invention are preferably formulated as pharmaceutical compositions administered by parenteral routes (e.g., subcutaneous, intravenous, intraperitoneal, intramuscular or transdermal). Such pharmaceutical compositions and processes for preparing same are well known in the art. (See, e.g., Remington: The Science and 50 Practice of Pharmacy (D. B. Troy, Editor, 21st Edition, Lippincott, Williams & Wilkins, 2006).

In another aspect, the polypeptides of the present invention or the pharmaceutically acceptable salts thereof for use as a medicament.

In another aspect, the polypeptides of the present invention or the pharmaceutically acceptable salts thereof for use in the treatment or prevention of a disease in a patient, wherein said disease is optionally selected from the group consisting of hyperglycemia, type 2 diabetes, impaired glucose tolerance, type 1 diabetes, obesity, hypertension, hyperlipidemia, syndrome X, dyslipidemia, cognitive disorders, atherosclerosis, myocardial infarction, coronary heart disease, stroke, inflammatory bowel syndrome, dyspepsia, alcoholism and gastric ulcers.

In another aspect, the polypeptide of the present invention or the pharmaceutically acceptable salts thereof may be provided simultaneously, separately, or sequentially in combination with an effective amount of one or more additional therapeutic agents.

In another aspect, the pharmaceutical composition according to the present invention comprise a polypeptide of the present invention or a pharmaceutically acceptable salt thereof for use as a medicament.

In another aspect, the pharmaceutical composition according to the present invention comprise a polypeptide of the present invention or a pharmaceutically acceptable salt thereof, for use in the treatment or prevention of a disease in a patient, wherein said disease is optionally selected from the group consisting of hyperglycemia, type 2 diabetes, impaired glucose tolerance, type 1 diabetes, obesity, hypertension, hyperlipidemia, syndrome X, dyslipidemia, cognitive disorders, atherosclerosis, myocardial infarction, coronary heart disease, stroke, inflammatory bowel syndrome, dyspepsia, alcoholism and gastric ulcers.

In another aspect, the pharmaceutical composition according to the present invention comprise a polypeptide of the present invention or a pharmaceutically acceptable salt thereof is provided simultaneously, separately, or sequentially in combination with an effective amount of one or more additional therapeutic agents.

The present invention may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

EXAMPLES

Instruments and analytical methods: Instruments used for characterization and analysis of the compounds of the present invention are HPLC (Waters e2695 Alliance; Detector Waters (2489 UV/Visible)).

Mass instrument: HPLC: Waters e2695 Alliance; Detector: Acquity-QDa.

The final compounds of the present disclosure were purified by preparative HPLC procedure as outlined below:

Preparative HPLC: WATERS 2555 Quaternary gradient module (Max Total Flow: 300 mL/min, Max Pressure: 3000 psi) or Shimadzu LC-8A (Max Total Flow: 150 mL, Max Pressure: 30 Mpa), Column: Phenyl, 10μ Flow: 75 mL/min Mobile Phase:

| | For first purification | For second purification | For third purification |
|---|---|---|---|
| Mobile Phase A | pH 8.0 Phosphate buffer | 1% Acetic acid in water | pH 8.2 Ammonium formate buffer |
| Mobile Phase B | Acetonitrile | 1% Acetic acid in Acetonitrile:n-Propanol (50:50) | Acetonitrile |
| Gradient | 15 to 45% Mobile Phase-B in 300 min | 20 to 50% Mobile Phase-B in 250 min | 20 to 50% Mobile Phase-B in 250 min |

The purity of the compounds of the present disclosure were analyzed by one of the RP-HPLC methods as outlined below:

HPLC Method A:

Column: Xbridge Peptide BEH C18 (4.6 mm×250 mm, 3.5μ)

Eluent: Mobile Phase A: Buffer:Acetonitrile (900:100)

Mobile phase B: Buffer:Acetonitrile (300:700)

Buffer: Potassium dihydrogen orthophosphate in water, pH adjusted to 3.0±0.1 with orthophosphoric acid Flow rate: 0.8 mL/min Detection: UV detection at 210 nm Column Temperature: 65° C.

Sample Tray temperature: 5° C.

Run Time: 90 min.

| Time (min) | Mobile Phase A % | Mobile Phase B % |
|---|---|---|
| 0 | 55 | 45 |
| 3 | 55 | 45 |
| 5 | 40 | 60 |
| 60 | 39 | 61 |
| 65 | 0 | 100 |
| 75 | 0 | 100 |

-continued

| Time (min) | Mobile Phase A % | Mobile Phase B % |
|---|---|---|
| 75.01 | 55 | 45 |
| 90 | 55 | 45 |

HPLC Method B:

Column: XSelect CSH C18 (4.6 mm×150 mm, 2.5μ)
Eluent: Mobile Phase A: Buffer:Acetonitrile (900:100)
Mobile phase B: Buffer:Acetonitrile (300:700)
Buffer: Potassium dihydrogen orthophosphate in water, pH adjusted to 3.0±0.1 with orthophosphoric acid
Flow rate: 0.8 mL/min
Detection: UV detection at 210 nm
Column Temperature: 65° C.
Sample Tray temperature: 5° C.
Run Time: 90 min.

| Time (min) | Mobile Phase A % | Mobile Phase B % |
|---|---|---|
| 0 | 55 | 45 |
| 3 | 55 | 45 |
| 5 | 40 | 60 |
| 60 | 39 | 61 |
| 65 | 0 | 100 |
| 75 | 0 | 100 |
| 75.01 | 55 | 45 |
| 90 | 55 | 45 |

HPLC Method C:

Column: Xbridge Peptide BEH C18 (4.6 mm×250 mm, 3.5μ)
Eluent: Mobile Phase A: Buffer:Acetonitrile (900:100)
Mobile phase B: Buffer:Acetonitrile (300:700)
Buffer: Potassium dihydrogen orthophosphate in water, pH adjusted to 3.0±0.1 with orthophosphoric acid
Flow rate: 1.0 mL/min
Detection: UV detection at 210 nm
Column Temperature: 65° C.
Sample Tray temperature: 5° C.
Run Time: 60 min.

| Time (min) | Mobile Phase A % | Mobile Phase B % |
|---|---|---|
| 0 | 55 | 45 |
| 2 | 41 | 59 |
| 50 | 40 | 60 |
| 51 | 55 | 45 |
| 60 | 55 | 45 |

HPLC Method D:

Column: XSelect CSH C18 (4.6 mm×150 mm, 2.5μ)
Eluent: Mobile Phase A: Buffer:Acetonitrile (900:100)
Mobile phase B: Buffer:Acetonitrile (300:700)
Buffer: Potassium dihydrogen orthophosphate in water, Added Triethylamine and pH adjusted to 2.5±0.1 with orthophosphoric acid
Flow rate: 0.5 mL/min
Detection: UV detection at 214 nm
Column Temperature: 60° C.
Sample Tray temperature: 10° C.
Run Time: 90 min.

| Time (min) | Mobile Phase A % | Mobile Phase B % |
|---|---|---|
| 0 | 55 | 45 |
| 6 | 55 | 45 |
| 10 | 40 | 60 |
| 80 | 39 | 61 |
| 80.1 | 0 | 100 |
| 85 | 0 | 100 |
| 85.1 | 55 | 45 |
| 90 | 55 | 45 |

Method of Preparation

Example 1: Preparation of 2-[2-[2-[[2-[[(4S)-5-tert-butoxy-4-[(20-tert-butoxy-20-oxo-icosanoyl)amino]-5-oxo-pentanoyl]amino]-2-methyl-propanoyl]amino]ethoxy]ethoxy]acetic acid (Moiety A-di-tert-butyl ester)

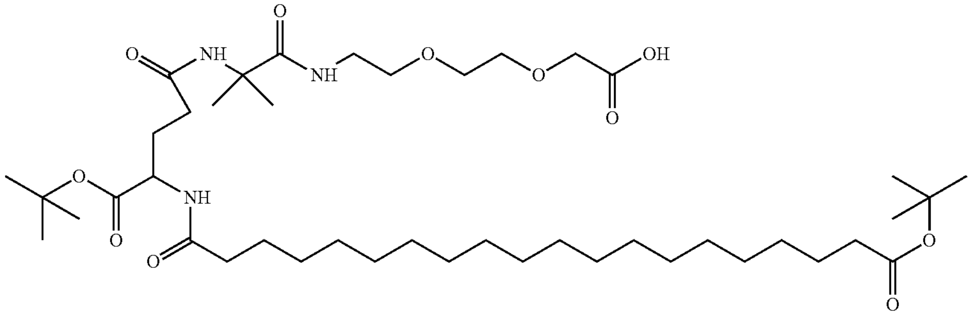

Moiety A-di-tert-butyl ester

Moiety A-di-tert-butyl ester was prepared using solid phase synthesis using 2-chlorotrityl chloride resin. 2-[2-(2-Fmoc-aminoethoxy)ethoxy]acetic acid was attached to 2-chlorotrityl chloride resin in presence of DIPEA to yield 2-[2-(2-Fmoc-aminoethoxy)ethoxy]acetic acid-2-Cl-Trt-Resin. The Fmoc protecting group was removed by selective de-blocking of amino group using piperidine followed by coupling with Fmoc-Aib-OH in THF using DIPC and HOBt which yielded 2-[2-[2-[(2-Fmoc-amino-2-methyl-propanoyl)amino]ethoxy]ethoxy]acetic acid-2-Cl-Trt-Resin. The Fmoc group was removed by selective de-blocking using piperidine and the free amino group was then coupled with Fmoc-Glu-OtBu using HOBt and DIPC to yield 2-[2-[2-[[2-[[(4S)-4-Fmoc-amino-5-tert-butoxy-5-oxo-pentanoyl]amino]-2-methyl-propanoyl]amino]ethoxy]ethoxy] acetic acid-2-Cl-Trt-Resin. The Fmoc group of the resultant compound was selectively de-blocked using piperidine and the free amino group was then coupled with 20-(tert-butoxy)-20-oxo-icosanoic acid to give 2-[2-[2-[2-[[(4S)-5-tert-butoxy-4-[(20-tert-butoxy-20-oxo-icosanoyl)amino]-5-oxo-pentanoyl]amino]-2-methyl-propanoyl]amino]ethoxy] ethoxy]acetic acid-2-Cl-Trt-Resin. This intermediate was then cleaved from 2-Cl-Trt-Resin using trifluoroethanol: DCM (1:1) to obtain 2-[2-[2-[[2-[(4S)-5-tert-butoxy-4-[(20-tert-butoxy-20-oxo-icosanoyl)amino]-5-oxo-pentanoyl] amino]-2-methyl-propanoyl]amino]ethoxy]ethoxy]acetic acid (Moiety A-di-tert-butyl ester). (LCMS=m/z: 814.10 $(M+H^+)$).

Example 2: Preparation of 2-[2-[2-[2-[[(4S)-5-tert-butoxy-4-[(18-tert-butoxy-18-oxo-octadecanoyl) amino]-5-oxo-pentanoyl]amino]-2-methyl-propanoyl]amino]ethoxy]ethoxy]acetic acid

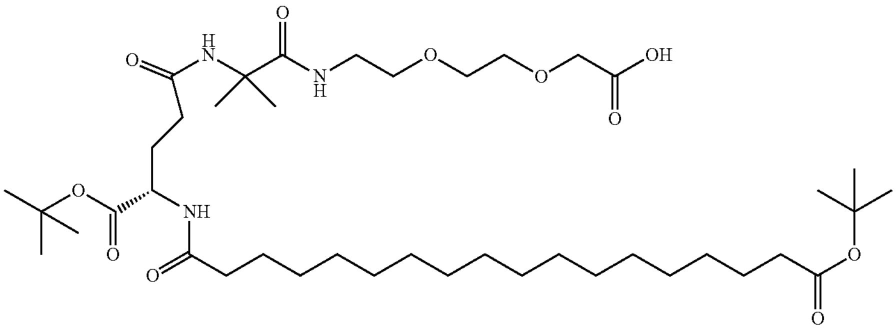

Moiety B-di-tert-butyl ester

Moiety B-di-tert-butyl ester was prepared using solid phase synthesis using 2-chlorotrityl chloride resin. 2-[2-(2-Fmoc-aminoethoxy)ethoxy]acetic acid was attached to 2-chlorotrityl chloride resin in presence of DIPEA to yield 2-[2-(2-Fmoc-aminoethoxy) ethoxy]acetic acid-2-Cl-Trt-Resin. The Fmoc protecting group was removed by selective de-blocking of amino group using piperidine followed by coupling with Fmoc-Aib-OH in THF using DIPC and HOBt which yielded 2-[2-[2-[(2-Fmoc-amino-2-methyl-propanoyl)amino]ethoxy]ethoxy]acetic acid-2-Cl-Trt-Resin. The Fmoc group was removed by selective de-blocking using piperidine and the free amino group was coupled with Fmoc-Glu-OtBu using HOBt and DIPC to yield 2-[2-[2-[2-[[(4S)-4-Fmoc-amino-5-tert-butoxy-5-oxo-pentanoyl] amino]-2-methyl-propanoyl]amino]ethoxy]ethoxy]acetic acid-2-Cl-Trt-Resin. The Fmoc group of the resultant compound was selectively de-blocked using piperidine and the free amino group was then coupled with octadecanedioic acid mono tert butyl ester to give 2-[2-[2-[2-[[(4S)-5-tert-butoxy-4-[(18-tert-butoxy-18-oxo-octadecanoyl)amino]-5-oxo-pentanoyl]amino]-2-methyl-propanoyl]-amino]ethoxy] ethoxy]acetic acid-2-Cl-Trt-Resin. The intermediate was then cleaved from 2-Cl-Trt-Resin using trifluoroethanol: DCM (1:1) to obtain 2-[2-[2-[2-[[(4S)-5-tert-butoxy-4-[(18-tert-butoxy-18-oxo-octadecanoyl)amino]-5-oxo-pentanoyl] amino]-2-methyl-propanoyl]amino]ethoxy]ethoxy]acetic acid (Moiety B-di-tert-butyl ester). (LCMS=m/z: 786.39 $(M+H^+)$).

Example 3: Preparation of 2-[2-[2-[[2-[2-[2-[[5-tert-butoxy-4-[(18-tert-butoxy-18-oxo-octadecanoyl) amino]-5-oxo-pentanoyl]amino]ethoxy]ethoxy] acetyl]amino]ethoxy]ethoxy]acetic acid (Moiety C-di-tert-butyl ester)

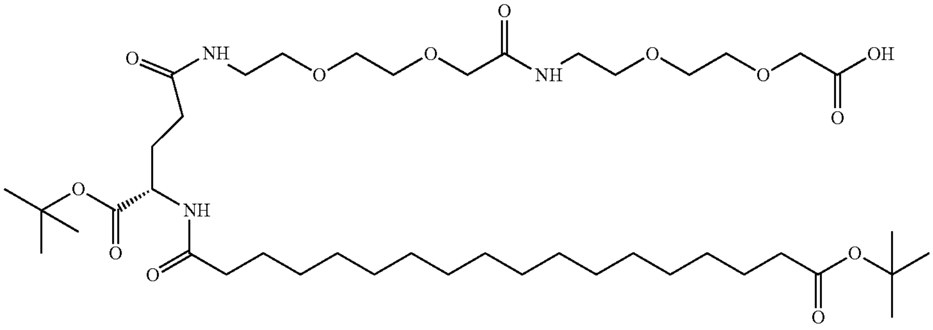

Moiety C-di-tert-butyl ester

Moiety C-di-tert-butyl ester was prepared using solid phase synthesis using 2-chlorotrityl chloride resin. 2-[2-(2-Fmoc-aminoethoxy) ethoxy]acetic acid was attached to 2-chlorotrityl chloride resin in presence of DIPEA to yield 2-[2-(2-Fmoc-aminoethoxy) ethoxy]acetic acid-2-Cl-Trt-Resin. The Fmoc protecting group was removed by selective de-blocking of amino group using piperidine followed by coupling with 2-[2-(2-Fmoc-aminoethoxy)ethoxy]acetic acid in THE using DIPC and HOBt which yielded {(Fmoc-amino-ethoxy)-ethoxy}-acetyl-{(-amino-ethoxy)-ethoxy}-acetic acid-2-Cl-Trt-Resin. The Fmoc group was removed by selective de-blocking using piperidine and the free amino group was coupled with Fmoc-Glu-OtBu using HOBt and DIPC to yield Fmoc-Glu({(amino-ethoxy)-ethoxy}-acetyl-{(-amino-ethoxy)-ethoxy}-acetic acid-2-Cl-Trt-Resin)-OtBu. The Fmoc group of the resultant compound was selectively de-blocked using piperidine and the free amino group was then coupled with octadecanedioic acid mono tert butyl ester to give 2-[2-[2-[[2-[2-[2-[5-tert-butoxy-4-[(18-tert-butoxy-18-oxo-octadecanoyl)amino]-5-oxo-pentanoyl] amino]ethoxy]ethoxy]acetyl]amino]ethoxy]ethoxy]acetic acid-2-Cl-Trt-Resin. The intermediate was then cleaved from 2-Cl-Trt-Resin using trifluoroethanol: DCM (1:1) to obtain 2-[2-[2-[[2-[2-[2[[5-tert-butoxy-4-[(18-tert-butoxy-18-oxo-octadecanoyl)amino]-5-oxo-pentanoyl]amino] ethoxy]ethoxy]acetyl]amino]ethoxy]ethoxy]acetic acid (Moiety C-di-tert-butyl ester) (LCMS=m/z: 846.10 ($M+H^+$)).

Example 4: Preparation of 2-[2-[2-[[2-[2-[2-[[5-tert-butoxy-4-[(20-tert-butoxy-20-oxo-icosanoyl)amino]-5-oxo-pentanoyl]amino]ethoxy]ethoxy]acetyl] amino]ethoxy]ethoxy]acetic acid Moiety D-di-tert-butyl Ester

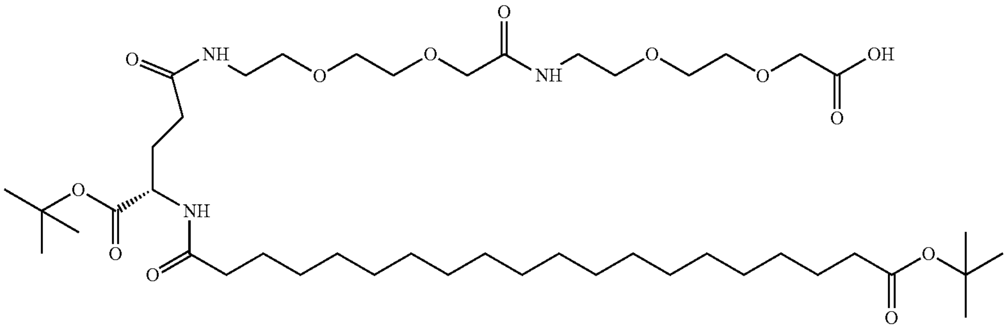

Moiety D-di-tert-butyl ester

Moiety D-di-tert-butyl ester was prepared using solid phase synthesis using 2-chlorotrityl chloride resin as schematically represented below. 2-[2-(2-Fmoc-aminoethoxy) ethoxy]acetic acid was attached to 2-chlorotrityl chloride resin in presence of DIPEA to yield 2-[2-(2-Fmoc-amino-ethoxy)ethoxy]acetic acid-2-Cl-Trt-Resin. The Fmoc protecting group was removed by selective de-blocking of amino group using piperidine followed by coupling with 2-[2-(2-Fmoc-aminoethoxy)ethoxy]acetic acid in THF using DIPC and HOBt which yielded {(Fmoc-amino-ethoxy)-ethoxy}-acetyl-{(-amino-ethoxy)-ethoxy}-acetic acid-2-Cl-Trt-Resin The Fmoc group was removed by selective de-blocking using piperidine and the free amino group was coupled with Fmoc-Glu-OtBu using HOBt and DIPC to yield Fmoc-Glu ({(amino-ethoxy)-ethoxy}-acetyl-{(-amino-ethoxy)-ethoxy}-acetic acid-2-Cl-Trt-Resin)-OtBu The Fmoc group of the resultant compound was selectively de-blocked using piperidine and the free amino group was then coupled with 20-(tert-Butoxy)-20-oxoicosanoic acid to give 2-[2-[2-[[2-[2-[2-[[5-tert-butoxy-4-[(20-tert-butoxy-20-oxo-icosanoyl)amino]-5-oxo-pentanoyl]amino]ethoxy] ethoxy]acetyl]amino]ethoxy]ethoxy]acetic acid-2-Cl-Trt-Resin. The intermediate was then cleaved from 2-Cl-Trt-Resin using trifluoroethanol: DCM (1:1) to obtain 2-[2-[2-[[2-[2-[2-[5-tert-butoxy-4-[(20-tert-butoxy-20-oxo-icosanoyl)amino]-5-oxo-pentanoyl]amino]ethoxy]ethoxy] acetyl]amino]ethoxy]ethoxy]acetic acid (Moiety D-di-tert-butyl ester) (LCMS=m/z: 874.15 (M+$H^+$)).

Example 5: Preparation of Compound 1

The parent peptide was synthesized by solid-phase method. The starting resin used for synthesis was Fmoc-Rink amide resin. Selective de-blocking of Fmoc protected amino group of rink amide resin was carried out using piperidine to yield Rink amide resin which was then coupled with Fmoc-Ser(tBu)-OH to yield Fmoc-Ser(tBu)-Rink amide Resin. This coupling reaction was performed by using diisopropylcarbodiimide. N-hydroxy benzotriazole (DIPC-HOBt) as coupling reagent. This completed one cycle. Acetic anhydride and diisopropylethyl amine/pyridine was used to terminate/cap the uncoupled amino groups at every amino acid coupling. Selective de-blocking of the amino group of Fmoc-Ser (tBu)-Rink amide Resin was done using piperidine. Then coupling with Fmoc-Pro-OH using HOBt and DIPC yielded Fmoc-Pro-Ser(tBu)-rink amide Resin. This completed the second cycle. Acetic anhydride and diisopropylethyl amine/pyridine were used to terminate the uncoupled amino groups at every amino acid coupling.

The above three steps, i.e., selective Capping, deblocking of Fmoc-protection of amino acid attached to the resin and coupling of next amino acid residue in sequence with Fmoc-protected amino group, were repeated for the remaining 37 amino acid residues. The selective deblocking, i.e., capping of uncoupled amino group done by using acetic anhydride and diisopropylethylamine/pyridine, deprotection of Fmoc group was done using piperidine and coupling with next Fmoc protected amino acid was done using HOBt/DIPC. The side chain of the Fmoc-protected amino acids were protected orthogonally, e.g., hydroxyl group of Serine. Tyrosine or Threonine were protected with tert-butyl(-tBu) group, amino group of Lysine was protected with tert-butyloxycarbonyl(-Boc) and (4,4-dimethyl-2,6-dioxocyclohex-1-ylidene)-3-methylbutyl(IVDde) group respectively and carboxylic acid groups of aspartic acid or glutamic acid were protected with -tBu group and amide group of glutamine was protected with trityl (-Trt) group. The above mentioned three steps. i.e., selective capping, deblocking and then coupling with next Fmoc protected amino acid, were performed to get Fmoc-Tyr(tBu)-Aib-Glu(OtBu)-Gly-Thr(tBu)-Phe-Thr(tBu)-Ser(tBu)-Asp(OtBu)-Tyr(tBu)-Ser(tBu)-Ile-[L-norvaline]-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser(tBu)-Gly-Ala-Pro-Pro-Pro-Ser(tBu)-resin.

De-blocking of Fmoc-Tyr(tBu)-Aib-Glu(OtBu)-Gly-Thr(tBu)-Phe-Thr(tBu)-Ser(tBu)-Asp(OtBu)-Tyr(tBu)-Ser(tBu)-Ile-[L-norvaline]-Leu-Asp(OtBu)-Lys(Boc)-Ile-Ala-Gln Trt)-Lys(IVDde)-Ala-Phe-Val-Gln(Trt)-Trp-Leu-Ile-Ala-Gly-Gly-Pro-Ser(tBu)-Ser(tBu)-Gly-Ala-Pro-Pro-Pro-Ser(tBu)-resin was carried out using piperidine followed by Boc protection of peptide resin using Boc anhydride to yield Boc-Tyr(tBu)-Aib-Glu(OtBu)-Gly-Thr(tBu)-Phe-Thr(tBu)-Ser(tBu)-Asp(OtBu)-Tyr(tBu)-Ser(tBu)-Ile-[L-norvaline]-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser(tBu)-Gly-Ala-Pro-Pro-Pro-Ser(tBu)-resin. De-protection of the IVDde group of the peptide resin was carried out using hydrazine hydrate and then it was coupled with Moiety A-di-tert-butyl ester using diisopropylcarbodiimide, N-hydroxy benzotriazole (DIPC-HOBt) as coupling reagent to yield an intermediate compound resin, Boc-Tyr(tBu)-Aib-Glu(OtBu)-Gly-Thr(tBu)-Phe-Thr(tBu)-Ser(tBu)-Asp(OtBu)-Tyr(tBu)-Ser(tBu)-Ile-[L-norvaline]-Leu-Asp(OtBu)-Lys(Boc)-Ile-Ala-Gln(Trt)-Lys(NH-Moiety A di-tert-butyl ester)-Ala-Phe-Val-Gln (Trt)-Trp-Leu-Ile-Ala-Gly-Gly-Pro-Ser(tBu)-Ser(tBu)-Gly-Ala-Pro-Pro-Pro-Ser(tBu)-resin, which on cleavage and de-protection using trifluoroacetic acid with ethane-1,2-dithiol and triisopropylsilane followed by purification through preparative HPLC resulted in Compound 1.

Mass (LCMS): m/z=1192.7 ($MH_4^{4+}$), Calculated Mass=4766.77: HPLC Purity (Method B): 98.60%, RT=33.8 min.

Example 6: Synthesis of Compound 2

Compound 2 was prepared by solid phase method as per the analogous process given for Example 5, wherein, Fmoc-[L-norvaline]-OH was used at position 2 instead of Fmoc-Aib-OH and Fmoc-Aib-OH was used at position $13^{th}$ instead of Fmoc-[L-norvaline]-OH to get Boc-Tyr(tBu)-[L-norvaline]-Glu(OtBu)-Gly-Thr(tBu)-Phe-Thr(tBu)-Ser(tBu)-Asp(OtBu)-Tyr(tBu)-Ser(tBu)-Ile-Aib-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser(tBu)-Gly-Ala-Pro-Pro-Pro-Ser(tBu)- resin.

Then coupling with Moiety A-di-tert-butyl ester followed by cleavage, de-protection and preparative HPLC purification as per Example 5 resulted in Compound 2.

Mass (LCMS): m/z=1192.6 ($MH_4^{4+}$), Calculated Mass=4766.4; HPLC Purity (Method B): 96.09%, RT=25.6 min.

Example 7: Synthesis of Compound 3

Compound 3 was prepared by solid phase method as per the analogous process given for Example 5, wherein Fmoc-Leu-OH was used at position 13 instead of Fmoc-[L-norvaline]-OH to get Boc-Tyr(tBu)-Aib-Glu(OtBu)-Gly-Thr(tBu)-Phe-Thr(tBu)-Ser(tBu)-Asp(OtBu)-Tyr(tBu)-Ser(tBu)-Ile-Leu-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser(tBu)-Gly- Ala-Pro-Pro-Pro-Ser(tBu)-resin.

Then coupling with Moiety A-di-tert-butyl ester followed by cleavage, de-protection and preparative HPLC purification as per Example 5 resulted in Compound 3.

Mass (LCMS): m/z=1196.1 ($MH_4^{4+}$), Calculated Mass=4780.4: HPLC Purity (Method A): 95.27%, RT=39.1 min.

Example 8: Synthesis of Compound 4

Compound 4 was prepared by solid phase method as per the analogous process given for Example 5, wherein Fmoc-

[L-norvaline]-OH was used at position 2 instead of Fmoc-Aib-OH to get Boc-Tyr (tBu)-[L-norvaline]-Glu(OtBu)-Gly-Thr(tBu)-Phe-Thr(tBu)-Ser(tBu)-Asp(OtBu)-Tyr(tBu)-Ser(tBu)-Ile-[L-norvaline]-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser(tBu)-Gly-Ala-Pro-Pro-Pro-Ser(tBu)-resin.

Then coupling with Moiety A-di-tert-butyl ester followed by cleavage, de-protection and preparative HPLC purification as per Example 5 resulted in compound 4.

Mass (LCMS): m/z=1196.32 ($MH_4^{4+}$), Calculated Mass=4781.25; HPLC Purity (Method A): 94.21%, RT=29.8 min.

Example 9: Synthesis of Compound 5

De-protection of IVDde group of peptide resin: Boc-Tyr (tBu)-Aib-Glu(OtBu)-Gly-Thr(tBu)-Phe-Thr(tBu)-Ser (tBu)-Asp(OtBu)-Tyr(tBu)-Ser(tBu)-Ile-[L-norvaline]-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser(tBu)-Gly-Ala-Pro-Pro-Pro-Ser(tBu)-resin (prepared as per Example 5) was carried out using hydrazine hydrate and then it was coupled with Moiety C-di-tert-butyl ester using diisopropylcarbodiimide, N-hydroxy benzotriazole (DIPC-HOBt) as coupling reagent to yield an intermediate compound resin, Boc-Tyr(tBu)-Aib-Glu(OtBu)-Gly-Thr(tBu)-Phe-Thr(tBu)-Ser(tBu)-Asp(OtBu)-Tyr(tBu)-Ser(tBu)-Ile-[L-norvaline]-Leu-Asp(OtBu)-Lys(Boc)-Ile-Ala-Gln(Trt)-Lys(NH-Moiety C di-tert-butyl ester)-Ala-Phe-Val-Gln (Trt)-Trp-Leu-Ile-Ala-Gly-Gly-Pro-Ser(tBu)-Ser(tBu)-Gly-Ala-Pro-Pro-Pro-Ser(tBu)-resin, which on cleavage and de-protection using trifluoroacetic acid with ethane-1,2-dithiol and triisopropylsilane followed by purification through preparative HPLC resulted in Compound 5.

Mass (LCMS): m/z=1600.80 ($MH_3^{3+}$), Calculated Mass=4799.376; HPLC Purity (Method A): 98.64%, RT=15.9 min.

Example 10: Synthesis of Compound 6

Compound 6 was prepared by solid phase method as per the analogous process given for Example 9, wherein coupling with Moiety D-di-tert-butyl ester was carried out, followed by cleavage, de protection and preparative HPLC purification as per Example 9 resulted in compound 6.

Mass (LCMS): m/z=1609.98 ($MH_3^{3+}$), Calculated Mass=4826.916:

HPLC Purity (Method A): 96.31%, RT=26.7 min.

Example 11: Synthesis of Compound 7

Compound 7 was prepared by solid phase method as per the analogous process given for Example 9, wherein coupling with Moiety B-di-tert-butyl ester carried out, followed by cleavage, de protection and preparative HPLC purification as per Example 9 resulted in compound 7.

Mass (LCMS): m/z=1580.64 ($MH_3^{3+}$), Calculated Mass=4738.896;

HPLC Purity (Method A): 98.43%, RT=18.5 min.

Example 12: Synthesis of Compound 8

The parent peptide was synthesized by solid-phase method. The starting resin used for the synthesis was Fmoc-Rink amide resin. Selectively de-blocking of Fmoc protected amino group of rink amide resin using piperidine followed by coupling with Fmoc-Lys (IVDde)-OH with the Rink amide resin. The coupling was performed by using DIPC-HOBt to yield Fmoc-Lys (IVDde)-Rink amide Resin, this completed one cycle. Acetic anhydride and diisopropylethyl amine/pyridine was used to terminate/cap the uncoupled amino groups at the end of every amino acid coupling. Selective de-blocking Fmoc of amino group of Fmoc-Lys(IVDde)-Rink amide Resin using piperidine, Then coupling with second amino acid i.e., Fmoc-Ser (tBu)-OH using HOBt and DIPC yielded Fmoc-Ser (tBu)-Lys (IVDde)-rink amide Resin. This completed the second cycle. As stated earlier acetic anhydride and diisopropylethyl amine/pyridine was used to terminate the uncoupled amino groups [Capping] after each amino acid coupling.

The above three steps, i.e., deblocking of Fmoc-protection of amino acid attached to the resin, coupling of next amino acid residue in sequence with Fmoc-protected amino group and selective Capping, were repeated for the remaining 38 amino acid residues. The side chain of the Fmoc-protected amino acids used were protected orthogonally, e.g., hydroxyl group of Serine. Tyrosine or Threonine were protected with tert-butyl(-tBu) group, amino group of Lysine was protected with tert-butyloxycarbonyl (-Boc) and (4,4-dimethyl-2,6-dioxocyclohex-1-ylidene)-3-methylbutyl (IVDde) group respectively and carboxylic acid groups of aspartic acid or glutamic acid were protected with -tBu group, amide group of glutamine and asparagine was protected with trityl (-Trt) group. The above mentioned three steps, i.e., selective capping, deblocking and then coupling with next Fmoc protected amino acid were performed to get Fmoc-Tyr(tBu)-Aib-Glu(OtBu)-Gly-Thr(tBu)-Phe-Thr (tBu)-Ser(tBu)-Asp(OtBu)-Tyr(tBu)-Ser(tBu)-Ile-L-Norvaline-Leu-Glu (OtBu)-Lys(Boc)-Ile-Ala-Ala-Gln(Trt)-Glu (OtBu)-Phe-Val-Asn(Trt)-Trp-Leu-Leu-Ala-Gly-Gly-Pro-Ser(tBu)-Ser(tBu)-Gly-Ala-Pro-Pro-Pro-Ser(tBu)-Lys (IVDde)-Rink amide resin.

De-blocking of Fmoc group from Fmoc-Tyr(tBu)-Aib-Glu(OtBu)-Gly-Thr(tBu)-Phe-Thr(tBu)-Ser(tBu)-Asp (OtBu)-Tyr(tBu)-Ser(tBu)-Ile-L-Norvaline-Leu-Glu(OtBu)-Lys(Boc)-Ile-Ala-Ala-Gln(Trt)-Glu(OtBu)-Phe-Val-Asn (Trt)-Trp-Leu-Leu-Ala- Gly-Gly-Pro-Ser(tBu)-Ser(tBu)-Gly-Ala-Pro-Pro-Pro-Ser(tBu)-Lys(IVDde)-Rink amide resin was done using piperidine followed by Boc protection of Peptide resin using Boc anhydride to yield Boc-Tyr(tBu)-Aib-Glu(OtBu)-Gly-Thr(tBu)-Phe-Thr(tBu)-Ser(tBu)-Asp (OtBu)-Tyr(tBu)-Ser(tBu)-Ile-L-Norvaline-Leu-Glu(OtBu)-Lys(Boc)-Ile-Ala-Ala-Gln(Trt)-Glu(OtBu)-Phe-Val-Asn (Trt)-Trp-Leu-Leu-Ala-Gly-Gly-Pro-Ser(tBu)-Ser(tBu)-Gly-Ala-Pro-Pro-Pro-Ser(tBu)-Lys(IVDde)-Rink amide resin.

De-protection of the IVDde group of peptide resin using Hydrazine hydrate followed by coupling of moiety-A-di-tert butyl ester was performed using diisopropylcarbodiimide, N-hydroxy benzotriazole (DIPC-HOBt) as the coupling reagent to yield protected compound 8-resin.

Boc-Tyr(tBu)-Aib-Glu(OtBu)-Gly-Thr(tBu)-Phe-Thr (tBu)-Ser(tBu)-Asp(OtBu)-Tyr(tBu)-Ser(tBu)-Ile-L-Norvaline-Leu-Glu(OtBu)-Lys(Boc)-Ile-Ala-Ala-Gln(Trt)-Glu (OtBu)-Phe-Val-Asn(Trt)-Trp-Leu-Leu-Ala-Gly-Gly-Pro-Ser(tBu)-Ser(tBu)- Gly-Ala-Pro-Pro-Pro-Ser(tBu)-Lys(NH moiety A-di-tert butyl ester)-Rink amide resin cleavage and de-protection using trifluoroacetic acid with ethane-1,2-dithiol and triisopropylsilane followed by purification through preparative HPLC resulted in Compound 8. The HPLC purity of Compound 8 was assessed by Method given below Mass (LCMS): m/z=980.42 ($MH_5^{5+}$), Calculated Mass=4897.06 HPLC Purity (Method D): 94.55%. RT=44.9 min.

Example 13: Synthesis of Compound 9

The parent peptide was synthesized by solid-phase method. The starting resin used for synthesis was Wang resin. Fmoc protected Arg(Pbf) was used for coupling with the Wang resin. The coupling was performed by using diisopropylcarbodiimide, N-hydroxybenzotriazole (DIC-HOBt) as coupling reagent in presence of 4-dimethylaminopyridine (DMAP) which yielded Fmoc-Arg(Pbf)-Wang Resin. Selective de-blocking of amino group of Fmoc-Arg (Pbf)-Wang Resin using piperidine followed by coupling with Fmoc-Ser(tBu)-OH using HOBt/DIPC yielded Fmoc-Ser(tBu)-Arg(Pbf)-Wang Resin. This completed one cycle. Acetic anhydride and diisopropylethyl amine/pyridine were used to terminate the uncoupled amino groups at every amino acid coupling.

The above two steps, i.e., selective deblocking of Fmoc-protection of amino acid attached to the resin and coupling of next amino acid residue in sequence with Fmoc-protected amino group were repeated for the remaining 38 amino acid residues. The side chain of the Fmoc-protected amino acids were protected orthogonally, e.g., hydroxyl group of Serine, Tyrosine or Threonine were protected with tert-butyl(-tBu) group, amino group of Lysine was protected with tert-butyloxycarbonyl(-Boc) and (4,4-dimethyl-2,6-dioxocyclohex-1-ylidene)-3-methylbutyl (IVDde) group respectively and carboxylic acid groups of aspartic acid or glutamic acid were protected with -tBu group. The above mentioned three steps, i.e., selective capping, deblocking and then coupling with next Fmoc protected amino acid were performed to get Fmoc-Tyr(tBu)-Aib-Glu(OtBu)-Gly-Thr(tBu)-Phe-Thr (tBu)-Ser(tBu)-Asp(OtBu)-Tyr(tBu)-Ser(tBu)-Ile-L-Norvaline-Leu-Asp(OtBu)-Lys(Boc)-Ile-Ala-Gln(Trt)-Lys (IVDde)-Ala-Phe-Val-Gln(Trt)-Trp-Leu-Ile-Ala-Gly-Gly-Pro- Ser(tBu)-Ser(tBu)-Gly-Ala-Pro-Pro-Pro-Ser(tBu)-Arg (Pbf)-Wang resin.

De-blocking of Fmoc-Tyr(tBu)-Aib-Glu(OtBu)-Gly-Thr (tBu)-Phe-Thr(tBu)-Ser(tBu)-Asp(OtBu)-Tyr(tBu)-Ser (tBu)-Ile-L-Norvaline-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro- Ser(tBu)-Ser(tBu)-Gly-Ala-Pro-Pro-Pro-Ser(tBu)-Arg(Pbf)-Wang resin, using piperidine followed by Boc protection of Peptide resin using Boc anhydride to yield Boc-Tyr(tBu)-Aib-Glu(OtBu)-Gly-Thr(tBu)-Phe-Thr(tBu)-Ser(tBu)-Asp(OtBu)-Tyr(tBu)-Ser(tBu)-Ile-L-Norvaline-Leu-Asp(OtBu)-Lys(Boc)-Ile-Ala-Gln(Trt)-Lys(IVDde)-Ala-Phe- Val-Gln(Trt)-Trp-Leu-Ile-Ala-Gly-Gly-Pro-Ser (tBu)-Ser(tBu)-Gly-Ala-Pro-Pro-Pro-Ser(tBu)-Arg(Pbf)-Wang resin. De-protection of IVDde group of peptide resin using Hydrazine hydrate followed by coupling of moiety A-di-tert butyl ester was performed by using diisopropylcarbodiimide, N-hydroxy benzotriazole (DIPC-HOBt) as coupling reagent to yield Compound 9-Wang resin.

Boc-Tyr(tBu)-Aib-Glu(OtBu)-Gly-Thr(tBu)-Phe-Thr (tBu)-Ser(tBu)-Asp(OtBu)-Tyr(tBu)-Ser(tBu)-Ile-L-Norvaline-Leu-Asp(OtBu)-Lys(Boc)-Ile-Ala-Gln(Trt)-Lys(NH moiety A-di-tert butyl ester)-Ala-Phe-Val-Gln(Trt)-Trp-Leu-Ile-Ala-Gly-Gly-Pro-Ser(tBu)-Ser(tBu)-Gly-Ala-Pro-Pro-Pro-Ser(tBu)-Arg(Pbf)-Wang resin.

Cleavage and de-protection from resin using trifluoroacetic acid with ethane-1,2-dithiol, triisopropylsilane followed by purification through preparative HPLC resulted in Compound 9. Mass (LCMS): m/z=985.88 ($MH_5^{5+}$), Calculated Mass=4924.36 HPLC Purity (Method C): 93.52%, RT=27.8 min.

Example 14: Synthesis of Compound 10

Compound 10 was prepared by solid phase method as per the analogous process given for Example 5, wherein, Fmoc-[2-amino butyric acid] was used at position 13 instead of Fmoc-[L-norvaline]-OH to get Boc-Tyr(tBu)-Aib-Glu (OtBu)-Gly-Thr(tBu)-Phe-Thr(tBu)-Ser(tBu)-Asp(OtBu)-Tyr(tBu)-Ser(tBu)-Ile-2-amino butyric acid-Leu-Asp (OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser (tBu)-Gly-Ala-Pro-Pro-Pro-Ser(tBu)-resin.

Then coupling with Moiety A-di-tert-butyl ester followed by cleavage, de-protection and preparative HPLC purification as per Example 5 resulted in Compound 10.

Mass (LCMS): m/z=1189.57 ($MH_4^{4+}$), Calculated Mass=4754.248; HPLC Purity (Method D): 96.79%, RT=42.6 min.

Example 15: Synthesis of Compound 11

Compound 11 was prepared by solid phase method as per the analogous process given for Example 5, wherein, Fmoc-norleucine was used at position 13 instead of Fmoc-[L-norvaline]-OH to get Boc-Tyr(tBu)-Aib-Glu(OtBu)-Gly-Thr(tBu)-Phe-Thr(tBu)-Ser(tBu)-Asp(OtBu)-Tyr(tBu)-Ser (tBu)-Ile-Norleucine-Leu-Asp(OtBu)-Lys(Boc)-Ile-Ala-Gln (Trt)-Lys(IVDde)-Ala-Phe-Val-Gln(Trt)-Trp-Leu-Ile-Ala-Gly-Gly-Pro-Ser(tBu)- Ser(tBu)-Gly-Ala-Pro-Pro-Pro-Ser (tBu)-resin.

Then coupling with Moiety A-di-tert-butyl ester followed by cleavage, de-protection and preparative HPLC purification as per Example 5 resulted in Compound 11. Mass (LCMS): m/z=1196.66 ($MH_4^{4+}$), Calculated Mass=4782.608: HPLC Purity (Method D): 95.43%, RT=58.7 min.

Example 16: Synthesis of Compound 12

Compound 12 was prepared by solid phase method as per the analogous process given for Example 5, wherein, Fmoc-Ile-OH was used at position 13 instead of Fmoc-[L-norvaline]-OH to get Boc-Tyr(tBu)-Aib-Glu(OtBu)-Gly-Thr (tBu)-Phe-Thr(tBu)-Ser(tBu)-Asp(OtBu)-Tyr(tBu)-Ser (tBu)-Ile-Ile-Leu-Asp(OtBu)-Lys(Boc)-Ile-Ala-Gln(Trt)-Lys(IVDde)-Ala-Phe-Val-Gln(Trt)-Trp-Leu-Ile-Ala-Gly-Gly-Pro-Ser(tBu)-Ser(tBu)-Gly- Ala-Pro-Pro-Pro-Ser(tBu)-resin.

Then coupling with Moiety A-di-tert-butyl ester followed by cleavage, de-protection and preparative HPLC purification as per Example 5 resulted in Compound 12.

Mass (LCMS): m/z=1196.32 ($MH_4^{4+}$), Calculated Mass=4781.25: HPLC Purity (Method D): 94.38%, RT=47.7 min.

Biological Studies

Example 12: Efficacy Study in db/db Mice at 10 nM/kg Dose

The effect of compounds of present invention on blood glucose, food intake and body weight was studied in mice. This study was performed in a type 2 diabetic mouse (db/db) model. The animals were divided into 4 treatment groups (n=6)—a diabetic control group, Compound 1 (10 nM/kg), Compound 2 (10 nM/kg) and Tirzepatide (10 nM/kg). Baseline blood glucose was measured from all the animals. All the animals were administered with test items subcutaneously. Blood glucose was measured at 4 hr, 8 hr, 12 hr, 24 hr, 48 hr, 72 hr and 96 hr post treatment. Delta blood glucose (mM) was calculated. The results are provided in Table 3. Similarly, body weight changes and cumulative food consumption was measured at 48 hr and 96 hr post treatment. The results of body weight changes are provided in Table 4 and cumulative food consumption are provided in Table 5. Similarly, the efficacy of Compounds 3, 4, 5, 6 and 7 in db/db mice at 10 nM/kg dose was carried out in separate study. The animals were divided into 7 treatment groups (n=6)—a diabetic control group, Compound 1, Compound 3, Compound 4, Compound 5, Compound 6 and Compound 7. Baseline blood glucose was measured from all the animals. All the animals were administered with test items subcutaneously. Blood glucose was measured at 4 hr, 8 hr, 12 hr, 24 hr, 48 hr, 72 hr and 96 hr post treatment. Delta blood glucose (mM) was calculated. The results are also provided in Table 3. Similarly, body weight changes and cumulative food consumption was measured at 48 hr and 96 hr post treatment. The results of body weight changes are also provided in Table 4 and cumulative food consumption are also provided in Table 5. Similarly, the efficacy of Compound 8 and 9 in db/db mice at 10 nM/kg dose were carried out in a separate study. The animals were divided into 3 treatment groups (n=5)—a diabetic control group, Compound 8 and Compound 9. Baseline blood glucose was measured from all the animals. All the animals were administered with test items subcutaneously. Blood glucose was measured at 4 hr, 8 hr, 12 hr, 24 hr, 48 hr, 72 hr and 96 hr post treatment. Delta blood glucose (mM) was calculated. The results are provided in Table 3. Similarly, body weight changes and cumulative food consumption was measured at 48 hr and 96 hr post treatment. The results of body weight changes are provided in Table 4 and cumulative food consumption are provided in Table 5. Another separate efficacy study for Compound 10, 11 and 12 in db/db mice at 10 nM/kg dose were carried out. The animals were divided into 4 treatment groups (n=5)—a diabetic control group, Compound 10, Compound 11 and Compound 12. Baseline blood glucose was measured from all the animals. All the animals were administered with test items subcutaneously. Blood glucose was measured at 4 hr, 8 hr, 12 hr, 24 hr, 48 hr, 72 hr and 96 hr post treatment. Delta blood glucose (mM) was calculated. The results are provided in Table 3. Similarly, body weight changes and cumulative food consumption was measured at 48 hr and 96 hr post treatment. The results of body weight changes are provided in Table 4 and cumulative food consumption are provided in Table 5.

TABLE 3

Effect on blood glucose
Delta Blood Glucose (mM) Mean (±SD)

Study 1

| Treatment Groups (n = 6) | 0 hr | 4 hr | 8 hr | 12 hr | 24 hr | 48 hr | 72 hr | 96 hr |
|---|---|---|---|---|---|---|---|---|
| Diabetic Control | 0 | 1.0 (±3.3) | 1.4 (±3.3) | 4.6 (±3.7) | 2.8 (±2.0) | 5.3 (±3.6) | 4.5 (±5.4) | 5.6 (±3.5) |
| Compound 1, 10 nM/kg/s.c | 0 | −12.7*** (±3.2) | −12.0*** (±3.9) | −10.5*** (±3.1) | −15.5*** (±4.0) | −6.7*** (±2.0) | −4.3*** (±3.0) | −2.2*** (±3.0) |
| Compound 2, 10 nM/kg/s.c | 0 | −7.4*** (±4.0) | −7.6*** (±1.8) | −9.7*** (±4.3) | −9.5*** (±4.0) | −3.6*** (±2.2) | −2.1** (±2.0) | −1.1** (±2.6) |
| Tirzepatide, 10 nM/kg/s.c | 0 | −9.9*** (±5.1) | −8.7*** (±1.2) | −8.6*** (±3.2) | −11.4*** (±3.9) | −5.3*** (±2.2) | −3.7*** (±1.4) | 3.7 (±1.8) |

Study 2

| Treatment Groups (n = 6) | 0 hr | 4 hr | 8 hr | 12 hr | 24 hr | 48 hr | 72 hr | 96 hr |
|---|---|---|---|---|---|---|---|---|
| Diabetic Control | 0 | 1.1 (±3.0) | 0.8 (±2.5) | 1.2 (±1.8) | 0.8 (±2.3) | 2.2 (±2.0) | 2.7 (±0.8) | 2.7 (±2.3) |
| Compound 3, 10 nM/kg/s.c/ single dose | 0 | −10.3*** (±3.2) | −13.9*** (±3.5) | −15.8*** (±3.7) | −10.9*** (±5.7) | −6.6*** (±8.0) | 0.1 (±2.1) | −0.7 (±2.9) |
| Compound 4, 10 nM/kg/s.c/ single dose | 0 | −10.4*** (±6.0) | −13.3*** (±4.5) | −13.8*** (±6.4) | −4.9* (±3.7) | −3.7* (±4.7) | 0.2 (±2.5) | −1.9 (±5.4) |
| Compound 5, 10 nM/kg/s.c/ single dose | 0 | −10.7*** (±4.8) | −11.9*** (±6.5) | −11.6*** (±7.2) | −7.2** (±7.4) | −2.8 (±4.8) | −0.8 (±2.0) | 0.9 (±1.8) |
| Compound 6, 10 nM/kg/s.c/ single dose | 0 | −15.6*** (±4.7) | −15.9*** (±5.6) | −16.3*** (4.4) | −11.8*** (±4.4) | −9.5*** (±6.6) | −2.6* (±2.9) | −1.6 (±2.3) |
| Compound 7, 10 nM/kg/s.c/ single dose | 0 | −8.5*** (±2.4) | −8.0*** (±5.7) | −4.1 (3.7) | −1.8 (±3.6) | −0.7 (±1.3) | −1.0 (±1.5) | −0.7 (±0.9) |
| Compound 1, 10 nM/kg/s.c/ single dose | 0 | −10.0*** (±3.0) | −13.5*** (±1.4) | −12.3*** (±1.8) | −11.5*** (±5.0) | −7.9*** (±3.8) | −4.3** (±1.4) | −1.4 (±3.1) |

Study 3

| Treatment Groups (n = 5) | 0 hr | 4 hr | 8 hr | 12 hr | 24 hr | 48 hr | 72 hr | 96 hr |
|---|---|---|---|---|---|---|---|---|
| Diabetic Control | 0 | −0.1 (±1.2) | 0.1 (±2.8) | 2.1 (±1.7) | 0.7 (±4.1) | 1.2 (±1.8) | 1.0 (±2.2) | 1.1 (±2.3) |
| Compound 8, 10 nM/kg/s.c/ single dose | 0 | −13.6*** (±2.5) | −13.6*** (±3) | −13.6*** (±3.5) | −8.5*** (±2.7) | −5.6* (±2.1) | −1.8 (±2.4) | −0.6 (±2.3) |

TABLE 3-continued

| Effect on blood glucose Delta Blood Glucose (mM) Mean (±SD) | | | | | | | | |
|---|---|---|---|---|---|---|---|---|
| Compound 9, 10 nM/kg/s.c/ single dose | 0 | −13.1*** (±3.6) | −12.7*** (±1.8) | −12.1*** (±2.5) | −8.7*** (±2.2) | −7.1*** (±2) | −5.6* (±2.6) | 0 (±2.9) |
| Study 4 | | | | | | | | |
| Treatment Groups (n = 5) | 0 hr | 4 hr | 8 hr | 12 hr | 24 hr | 48 hr | 72 hr | 96 hr |
| Diabetic Control | 0 | 0.2 (±2.7) | 1.2 (±2.4) | 2.2 (±3.3) | 1.7 (±3.1) | 2.5 (±2.4) | 3.6 (±4) | 7 (±1.7) |
| Compound 10, 10 nM/kg/s.c/ single dose | 0 | −12.1*** (±3.1) | −13.6*** (±3.2) | −14.7*** (±2.9) | −15.6*** (±3.5) | −4.0** (±3.8) | 2.3 (±1.8) | 1.7 (±2.7) |
| Compound 11, 10 nM/kg/s.c/ single dose | 0 | −13.3*** (±4.4) | −13.3*** (±3.8) | −13.6*** (±3.2) | −15.4*** (±3.8) | −6.1*** (±4.5) | 3.6 (±3.6) | 6 (±2.7) |
| Compound 12, 10 nM/kg/s.c/ single dose | 0 | −14.6*** (±0.7) | −14.8*** (±1.3) | −14.9*** (±1.9) | −4.8** (±2.3) | 2.5 (±3.6) | 3.9 (±3.2) | 6.8 (±1.8) |

*p < 0.05, p < 0.01, *p < 0.001 vs Diabetic Control; Two way ANOVA followed by Bonferroni's post-test.

TABLE 4

| Effect on body weight | Body Wt. Change (%) 48 hr. vs. Baseline | | Body Wt. Change (%) 96 hr. vs. Baseline | |
|---|---|---|---|---|
| | Mean | SD | Mean | SD |
| Study 1 | | | | |
| Treatment Groups (n = 6) | | | | |
| Diabetic Control | 1.0 | 0.5 | 1.4 | 0.5 |
| Compound 1, 10 nM/kg/s.c | −5.1*** | 0.3 | −4.2*** | 0.9 |
| Compound 2, 10 nM/kg/s.c | −4.3*** | 0.7 | −3.3*** | 1.3 |
| Tirzepatide, 10 nM/kg/s.c | −4.2*** | 0.8 | −2.8*** | 0.9 |
| Study 2 | | | | |
| Diabetic Control | 1.8 | 1.6 | 4.1 | 3.5 |
| Compound 3, 10 nM/kg/s.c/single dose | −5.6*** | 0.8 | −4.9*** | 1.4 |
| Compound 4, 10 nM/kg/s.c/single dose | −3.8*** | 1.0 | −1.9** | 1.3 |
| Compound 5, 10 nM/kg/s.c/single dose | −4.6*** | 4.0 | −3.3*** | 6.0 |
| Compound 6, 10 nM/kg/s.c/single dose | −5.5*** | 2.0 | −2.2** | 1.3 |
| Compound 7, 10 nM/kg/s.c/single dose | −4.8*** | 0.5 | −2.9*** | 1.1 |
| Compound 1, 10 nM/kg/s.c/single dose | −5.1*** | 1.2 | −3.5*** | 0.7 |
| Study 3 | | | | |
| Treatment Groups (n = 5) | | | | |
| Diabetic Control | 1.1 | 0.7 | 1.8 | 1.0 |
| Compound 8, 10 nM/kg/s.c/single dose | −3.1*** | 1.0 | −2.8*** | 1.3 |
| Compound 9, 10 nM/kg/s.c/single dose | −3.4*** | 0.6 | −3.8*** | 0.5 |
| Study 4 | | | | |
| Diabetic Control | 0.9 | 1.7 | 0.9 | 1.0 |
| Compound 10, 10 nM/kg/s.c/single dose | −4.5*** | 0.6 | −3.1*** | 0.9 |
| Compound 11, 10 nM/kg/s.c/single dose | −4.7*** | 1.8 | −2.0*** | 1.1 |

TABLE 4-continued

| Effect on body weight | Body Wt. Change (%) 48 hr. vs. Baseline | | Body Wt. Change (%) 96 hr. vs. Baseline | |
|---|---|---|---|---|
| | Mean | SD | Mean | SD |
| Compound 12, 10 nM/kg/s.c/single dose | −3.0*** | 1.7 | −0.4 | 2.5 |

*p < 0.05,
**p < 0.01,
***p < 0.001 vs. Diabetic Control;
One way ANOVA followed by Bonferroni's post test.

TABLE 5

| Effect on food consumption | Cumulative food Intake (g) 0-48 hr. vs. Baseline | | Cumulative food Intake (g) 0-96 hr. vs. Baseline | |
|---|---|---|---|---|
| | Mean | SD | Mean | SD |
| Study 1 | | | | |
| Treatment Groups (n = 6) | | | | |
| Diabetic Control | 11.7 | 1.6 | 24.6 | 4.0 |
| Compound 1, 10 nM/kg/s.c | 7.5*** | 2.0 | 13.9*** | 2.4 |
| Compound 2, 10 nM/kg/s.c | 6.5*** | 0.1 | 21.6 | 1.1 |
| Tirzepatide, 10 nM/kg/s.c | 4.9*** | 1.4 | 13.0*** | 1.3 |
| Study 2 | | | | |
| Diabetic Control | 12.0 | 0.1 | 25.8 | 4.9 |
| Compound 3, 10 nM/kg/s.c/single dose | 6.0*** | 4.8 | 16.0*** | 3.8 |
| Compound 4, 10 nM/kg/s.c/single dose | 4.6*** | 2.4 | 14.4*** | 4.3 |
| Compound 5, 10 nM/kg/s.c/single dose | 6.2*** | 1.6 | 18.4** | 4.5 |
| Compound 6, 10 nM/kg/s.c/single dose | 4.2*** | 1.5 | 16.0*** | 3.6 |
| Compound 7, 10 nM/kg/s.c/single dose | 5.6*** | 0.7 | 19.6* | 0.3 |
| Compound 1, 10 nM/kg/s.c/single dose | 3.8*** | 0.7 | 12.5*** | 2.5 |

TABLE 5-continued

| Effect on food consumption | | | | |
|---|---|---|---|---|
| | Cumulative food Intake (g) 0-48 hr. vs. Baseline | | Cumulative food Intake (g) 0-96 hr. vs. Baseline | |
| | Mean | SD | Mean | SD |
| Study 3 | | | | |
| Treatment Groups (n = 5) | | | | |
| Diabetic Control | 14.9 | 0.5 | 29.8 | 1.2 |
| Compound 8, 10 nM/kg/s.c/single dose | 4.0*** | 1.0 | 13.9*** | 1.6 |
| Compound 9, 10 nM/kg/s.c/single dose | 4.2*** | 0.9 | 16.7*** | 3.4 |
| Study 4 | | | | |
| Diabetic Control | 14.4 | 0.8 | 25.7 | 0.4 |
| Compound 10, 10 nM/kg/s.c/single dose | 8.2*** | 2.2 | 20.5** | 3.9 |
| Compound 11, 10 nM/kg/s.c/single dose | 8.2*** | 1.1 | 21.7* | 1.0 |
| Compound 12, 10 nM/kg/s.c/single dose | 10.2* | 0.7 | 26.0 | 0.5 |

*p < 0.05,
**p < 0.01,
***p < 0.001 vs. Diabetic Control;
One way ANOVA followed by Bonferroni's post test.

The results demonstrate that Compound 1 and Compound 2 showed statistically significant blood glucose reduction upto 96 hr post treatment. The effect on blood glucose reduction for the compounds was superior to tirzepatide when tested at the same concentration.

Compound 1 and Compound 2 also showed statistically significant body weight reduction which was comparable to tirzepatide. Compound 1 showed a significant reduction in food consumption which was comparable to tirzepatide. No significant reduction in food consumption was observed for Compound 2 as compared to diabetic control.

Similarly the results demonstrate that Compounds 3, 4, 5, 6 and 7 of present invention showed statistically significant blood glucose reduction upto 96 hr post treatment. Also statistically significant reduction in food intake and body weight was observed for these compounds compared to diabetic control.

Example 13: Efficacy Study in db/db Mice at 3 and 20 nM/kg Dose

The effect of compounds of present invention on blood glucose, food intake and body weight was studied on mice. This study was performed in type 2 diabetic mouse (db/db) model. The animals were divided into 5 treatment groups (n=8)—a diabetic control group, Compound 1 (3 nM/kg and 20 nM/kg) and Tirzepatide (3 nM/kg and 20 nM/kg). Baseline blood glucose was measured from all the animals. All animals were administered with test items subcutaneously. Blood glucose was measured at 4 hr, 24 hr, 48 hr, 72 hr post treatment. Delta blood glucose (mM) was calculated. Body weight changes and cumulative food consumption was measured at 72 hr post treatment. The results of delta blood glucose are provided in Table 6. Similarly the results of body weight changes are provided in Table 7 and food consumption are provided in Table 8.

TABLE 6

| Effect of Compound 1 on blood glucose | | | | | |
|---|---|---|---|---|---|
| Treatment | Delta Blood Glucose (mM), Mean (±SD) | | | | |
| Groups (n = 8) | 0 hr | 4 hr | 24 hr | 48 hr | 72 hr |
| Diabetic Control | 0.0 | −0.1 (±1.9) | 0.9 (±1.6) | 0.1 (±1.2) | 0.3 (±1.8) |
| Compound 1, 3 nM/kg/s.c | 0.0 | −8.9*** (±3.1) | −9.9*** (±4.7) | −5.8** (±3.4) | −3.2 (±2.3) |
| Compound 1, 20 nM/kg/s.c | 0.0 | −13.7*** (±3.1) | −13.6*** (±5.9) | −14.0*** (±6.6) | −7.9*** (±4.9) |
| Tirzepatide, 3 nM/kg/s.c | 0.0 | −4.4* (±3.2) | −1.6 (±2.9) | 0.7 (±1.8) | 1.4 (±1.8) |
| Tirzepatide, 20 nM/kg/s.c | 0.0 | −8.2*** (±3.6) | −11.1*** (±4.0) | −7.6*** (±4.7) | −1.3 (±2.1) |

*p < 0.05,
**p < 0.01,
***p < 0.001 vs. Diabetic Control;
Two way ANOVA followed by Bonferroni's post-test.

TABLE 7

| Effect of Compound 1 on body weight | | |
|---|---|---|
| Treatment Groups | Body weight change (%) 72 hr vs. Baseline | |
| (n = 8) | Mean | SD |
| Diabetic Control | 1.3 | 1.1 |
| Compound 1, 3 nM/kg/s.c | −4.0*** | 0.7 |
| Compound 1, 20 nM/kg/s.c | −6.2*** | 1.4 |
| Tirzeatide, 3 nM/kg/s.c | −3.4*** | 2.2 |
| Tirzepatide, 20 nM/kg/s.c | −4.9*** | 0.8 |

*p < 0.05,
**p < 0.01,
***p < 0.001 vs. Diabetic Control;
One way ANOVA followed by Bonferroni's post test

TABLE 8

| Effect of Compound 1 on food consumption | | |
|---|---|---|
| Treatment Groups | Cumulative Food Intake (g), 0-72 hr | |
| (n = 8) | Mean | SD |
| Diabetic Control | 16.4 | 1.40 |
| Compound 1, 3 nM/kg/s.c | 10.2*** | 1.66 |
| Compound 1, 20 nM/kg/s.c | 6.3*** | 1.03 |
| Tirzepatide, 3 nM/kg/s.c | 9.6*** | 1.71 |
| Tirzepatide, 20 nM/kg/s.c | 8.4*** | 2.16 |

*p < 0.05,
**p < 0.01,
***p < 0.001 vs. Diabetic Control;
one way ANOVA followed by Bonferroni's post test The results demonstrate that Compound 1 at 3 nM/kg and 20 nM/kg showed dose dependent improvement in glucose lowering effect upto 72 hours. The effect was superior to tirzepatide at similar dosage.

The effect compound 1 on food intake and body weight at 3 and 20 nM/kg dose was significant, dose dependent and comparable to tirzepatide.

The results presented above demonstrate that the compounds of present invention are potent inhibitors of GLP-1 and GIP receptors and can be effective in treatment of type 2 diabetes, diabetes with obesity, obesity and hyperlipidemia.

Example 16: Cellular CAMP Assay

In-vitro potency determination was performed using a cAMP assay. G protein coupled receptor (GPCR) activation following ligand binding initiates a series of second messenger cascades that results in a cellular response. Signaling by the GLP-1R and GIP-R involves activation of adenylate cyclase and cAMP production. Cellular cAMP production was determined using the CAMP Hunter™ eXpress GPCR Assay (Eurofins DiscoveRx).

Cellular CAMP Assay of tirzepatide, Compound 1, Compound 3, Compound 6, Compound 10 and Compound 11 was performed and the half effective concentrations on GLP-1R-expressing cells and GIPR-expressing cells was as mentioned in below Table 9:

TABLE 9

Half-effective concentrations on GLP-1R-expressing cells and GIPR-expressing cells

| Compound | Half effective Concentration (EC50) GLP-1R | Half effective Concentration (EC50) GIPR | Half effective Concentration (EC50) GLP-1R (Exenatide) | Half effective Concentration (EC50) GIPR (GIP) |
|---|---|---|---|---|
| Tirzepatide | 6.8 nM | 1.9 nM | 78.9 pM | 306.1 pM |
| Compound 1 | 12.4 pM | 27.6 pM | 35.9 pM | 179.2 pM |

TABLE 9-continued

Half-effective concentrations on GLP-1R-expressing cells and GIPR-expressing cells

| Compound | Half effective Concentration (EC50) GLP-1R | Half effective Concentration (EC50) GIPR | Half effective Concentration (EC50) GLP-1R (Exenatide) | Half effective Concentration (EC50) GIPR (GIP) |
|---|---|---|---|---|
| Compound 3 | 32.7 pM | 12.8 pM | 87.3 pM | 41.1 pM |
| Compound 6 | 19.6 pM | 17.7 pM | | |
| Compound 10 | 3.6 pM | 7.3 pM | 15 pM | 50.4 pM |
| Compound 11 | 5.9 pM | 6.4 pM | | |

SEQUENCE LISTING

```
Sequence total quantity: 13
SEQ ID NO: 1            moltype = AA  length = 46
FEATURE                 Location/Qualifiers
REGION                  1..46
                        note = Synthetic
REGION                  1..46
                        note = MISC_FEATURE - The acid group of the C terminal
                         amino acid is a free carboxylic acid or is amidated as
                         C-terminal primary amide
REGION                  1..46
                        note = MISC_FEATURE - at least one of X3 and X5 is Lys
REGION                  1..46
                        note = MISC_FEATURE - when X1 is Aib, X2 is not Aib
SITE                    2
                        note = MISC_FEATURE - Xaa = Aib (2-Aminoisobutyric acid),
                         L-norvaline or D-norvaline
SITE                    13
                        note = MISC_FEATURE - Xaa = Aib (2-Aminoisobutyric acid),
                         Leu, (D)-Leu, Val, (D)-Val, Ile, (D)-Ile or an modified
                         amino acid of Formula -[NH-CH(R)-C(O)]-
SITE                    15
                        note = MISC_FEATURE - Xaa = Asp or Glu
SITE                    19
                        note = MISC_FEATURE - Xaa = Gln or Ala
SITE                    20
                        note = MISC_FEATURE - Xaa = Gln or Lys; wherein, when Lys,
                         the side chain amino (Epsilon amino) group of Lys is
                         substituted
SITE                    21
                        note = MISC_FEATURE - Xaa = Ala or Glu
SITE                    24
                        note = MISC_FEATURE - Xaa = Gln or Asn
SITE                    27
                        note = MISC_FEATURE - Xaa = Leu, Ile or Glu
SITE                    40
                        note = MISC_FEATURE - Xaa = absent, Arg or Lys; wherein
                         when Lys, the side chain amino (Epsilon amino) group of
                         Lys is substituted
SITE                    41
                        note = MISC_FEATURE - Xaa = absent or Lys
SITE                    42
                        note = MISC_FEATURE - Xaa = absent or Lys
SITE                    43
                        note = MISC_FEATURE - Xaa = absent or Lys
SITE                    44
                        note = MISC_FEATURE - Xaa = absent or Lys
SITE                    45
                        note = MISC_FEATURE - Xaa = absent or Lys
```

-continued

```
SITE                    46
                        note = MISC_FEATURE - Xaa = absent or Lys
source                  1..46
                        mol_type = protein
                        organism = synthetic construct
SEQUENCE: 1
YXEGTFTSDY SIXLXKIAXX XFVXWLXAGG PSSGAPPPSX XXXXXX                46

SEQ ID NO: 2            moltype = AA  length = 46
FEATURE                 Location/Qualifiers
REGION                  1..46
                        note = Synthetic
REGION                  1..46
                        note = MISC_FEATURE - The acid group of the C terminal
                         amino acid is a free carboxylic acid or is amidated as
                         C-terminal primary amide
SITE                    2
                        note = MISC_FEATURE - Xaa = Aib (2-Aminoisobutyric acid)
SITE                    13
                        note = MISC_FEATURE - Xaa = Leu, Ile, L-norvaline,
                         L-homoalanine or L-norleucine
SITE                    20
                        note = MISC_FEATURE - Xaa = Lys, wherein the side chain
                         amino (Epsilon amino) group of Lys is substituted
SITE                    27
                        note = MISC_FEATURE - Xaa = Ile
SITE                    40
                        note = MISC_FEATURE - Xaa= absent or Arg
SITE                    41
                        note = MISC_FEATURE - Xaa = absent or Lys
SITE                    42
                        note = MISC_FEATURE - Xaa = absent or Lys
SITE                    43
                        note = MISC_FEATURE - Xaa = absent or Lys
SITE                    44
                        note = MISC_FEATURE - Xaa = absent or Lys
SITE                    45
                        note = MISC_FEATURE - Xaa = absent or Lys
SITE                    46
                        note = MISC_FEATURE - Xaa = absent or Lys
source                  1..46
                        mol_type = protein
                        organism = synthetic construct
SEQUENCE: 2
YXEGTFTSDY SIXLDKIAQX AFVQWLXAGG PSSGAPPPSX XXXXXX                46

SEQ ID NO: 3            moltype = AA  length = 39
FEATURE                 Location/Qualifiers
REGION                  1..39
                        note = Synthetic
REGION                  1..39
                        note = MISC_FEATURE - The acid group of the C terminal
                         amino acid is is a free carboxylic acid or is amidated as
                         C-terminal primary amide
REGION                  1..39
                        note = MISC_FEATURE - when X1 is Aib, X2 is not Aib
SITE                    2
                        note = MISC_FEATURE - Xaa = Aib (2-Aminoisobutyric acid) or
                         L-norvaline
SITE                    13
                        note = MISC_FEATURE - Xaa = Aib, Leu, Ile, L-norvaline,
                         L-homoalanine or L-norleucine
SITE                    20
                        note = MISC_FEATURE - Xaa = Lys, wherein the side chain
                         amino (Epsilon amino) group of Lys is substituted
SITE                    27
                        note = MISC_FEATURE - Xaa = Ile
source                  1..39
                        mol_type = protein
                        organism = synthetic construct
SEQUENCE: 3
YXEGTFTSDY SIXLDKIAQX AFVQWLXAGG PSSGAPPPS                        39

SEQ ID NO: 4            moltype = AA  length = 39
FEATURE                 Location/Qualifiers
REGION                  1..39
                        note = Synthetic
SITE                    2
                        note = MISC_FEATURE - Xaa = Aib (2-Aminoisobutyric acid)
```

-continued

```
SITE                    13
                        note = MISC_FEATURE - Xaa = L-Norvaline
SITE                    20
                        note = MISC_FEATURE - Side chain amino (Epsilon amino)
                         group of Lys is substituted
SITE                    39
                        note = MISC_FEATURE - Ser at position 39 is amidated as a
                         C-terminal primary amide
source                  1..39
                        mol_type = protein
                        organism = synthetic construct
SEQUENCE: 4
YXEGTFTSDY SIXLDKIAQK AFVQWLIAGG PSSGAPPPS                          39

SEQ ID NO: 5            moltype = AA  length = 39
FEATURE                 Location/Qualifiers
REGION                  1..39
                        note = Synthetic
SITE                    2
                        note = MISC_FEATURE - Xaa = L-Norvaline
SITE                    13
                        note = MISC_FEATURE - Xaa = Aib (2-Aminoisobutyric acid)
SITE                    20
                        note = MISC_FEATURE - Side chain amino (Epsilon amino)
                         group of Lys is substituted
SITE                    39
                        note = MISC_FEATURE - Ser at position 39 is amidated as a
                         C-terminal primary amide
source                  1..39
                        mol_type = protein
                        organism = synthetic construct
SEQUENCE: 5
YXEGTFTSDY SIXLDKIAQK AFVQWLIAGG PSSGAPPPS                          39

SEQ ID NO: 6            moltype = AA  length = 39
FEATURE                 Location/Qualifiers
REGION                  1..39
                        note = Synthetic
SITE                    2
                        note = MISC_FEATURE - Xaa = Aib (2-aminoisobutyric acid)
SITE                    20
                        note = MISC_FEATURE - Side chain amino (Epsilon amino)
                         group of Lys is substituted
SITE                    39
                        note = MISC_FEATURE - Ser at position 39 is amidated as a
                         C-terminal primary amide
source                  1..39
                        mol_type = protein
                        organism = synthetic construct
SEQUENCE: 6
YXEGTFTSDY SILLDKIAQK AFVQWLIAGG PSSGAPPPS                          39

SEQ ID NO: 7            moltype = AA  length = 39
FEATURE                 Location/Qualifiers
REGION                  1..39
                        note = Synthetic
SITE                    2
                        note = MISC_FEATURE - Xaa = L-Norvaline
SITE                    13
                        note = MISC_FEATURE - Xaa = L-Norvaline
SITE                    20
                        note = MISC_FEATURE - Side chain amino (Epsilon amino)
                         group of Lys is substituted
SITE                    39
                        note = MISC_FEATURE - Ser at position 39 is amidated as a
                         C-terminal primary amide
source                  1..39
                        mol_type = protein
                        organism = synthetic construct
SEQUENCE: 7
YXEGTFTSDY SIXLDKIAQK AFVQWLIAGG PSSGAPPPS                          39

SEQ ID NO: 8            moltype = AA  length = 40
FEATURE                 Location/Qualifiers
REGION                  1..40
                        note = Synthetic
SITE                    2
                        note = MISC_FEATURE - Xaa = Aib (2-Aminoisobutyric acid)
SITE                    13
```

```
                      note = MISC_FEATURE - Xaa = L-Norvaline
SITE                  40
                      note = MISC_FEATURE - Side chain amino (Epsilon amino)
                       group of Lys is substituted
SITE                  40
                      note = MISC_FEATURE - Lys at position 40 is amidated as a
                       C-terminal primary amide
source                1..40
                      mol_type = protein
                      organism = synthetic construct
SEQUENCE: 8
YXEGTFTSDY SIXLEKIAAQ EFVNWLLAGG PSSGAPPPSK                        40

SEQ ID NO: 9          moltype = AA  length = 40
FEATURE               Location/Qualifiers
REGION                1..40
                      note = Synthetic
SITE                  2
                      note = MISC_FEATURE - Xaa = Aib (2-Aminoisobutyric acid)
SITE                  13
                      note = MISC_FEATURE - Xaa = L-Norvaline
SITE                  20
                      note = MISC_FEATURE - Side chain amino (Epsilon amino)
                       group of Lys is substituted
source                1..40
                      mol_type = protein
                      organism = synthetic construct
SEQUENCE: 9
YXEGTFTSDY SIXLDKIAQK AFVQWLIAGG PSSGAPPPSR                        40

SEQ ID NO: 10         moltype = AA  length = 39
FEATURE               Location/Qualifiers
REGION                1..39
                      note = Synthetic
SITE                  2
                      note = MISC_FEATURE - Xaa = Aib (2-Aminoisobutyric acid)
SITE                  13
                      note = MISC_FEATURE - Xaa = L-homoalanine
SITE                  20
                      note = MISC_FEATURE - Side chain amino (Epsilon amino)
                       group of Lys is substituted
SITE                  39
                      note = MISC_FEATURE - Ser at position 39 is amidated as a
                       C-terminal primary amide
source                1..39
                      mol_type = protein
                      organism = synthetic construct
SEQUENCE: 10
YXEGTFTSDY SIXLDKIAQK AFVQWLIAGG PSSGAPPPS                         39

SEQ ID NO: 11         moltype = AA  length = 39
FEATURE               Location/Qualifiers
REGION                1..39
                      note = Synthetic
SITE                  2
                      note = MISC_FEATURE - Xaa = Aib (2-Aminoisobutyric acid)
SITE                  13
                      note = MISC_FEATURE - Xaa = L-Norleucine
SITE                  20
                      note = MISC_FEATURE - Side chain amino (Epsilon amino)
                       group of Lys is substituted
SITE                  39
                      note = MISC_FEATURE - Ser at position 39 is amidated as a
                       C-terminal primary amide
source                1..39
                      mol_type = protein
                      organism = synthetic construct
SEQUENCE: 11
YXEGTFTSDY SIXLDKIAQK AFVQWLIAGG PSSGAPPPS                         39

SEQ ID NO: 12         moltype = AA  length = 39
FEATURE               Location/Qualifiers
REGION                1..39
                      note = Synthetic
SITE                  2
                      note = MISC_FEATURE - Xaa = Aib (2-Aminoisobutyric acid)
SITE                  20
                      note = MISC_FEATURE - Side chain amino (Epsilon amino)
                       group of Lys is substituted
```

-continued

```
SITE                  39
                      note = MISC_FEATURE - Ser at position 39 is amidated as a
                       C-terminal primary amide
source                1..39
                      mol_type = protein
                      organism = synthetic construct
SEQUENCE: 12
YXEGTFTSDY SIILDKIAQK AFVQWLIAGG PSSGAPPPS                          39

SEQ ID NO: 13         moltype = AA  length = 39
FEATURE               Location/Qualifiers
source                1..39
                      mol_type = protein
                      organism = synthetic construct
SITE                  2
                      note = MISC_FEATURE - Xaa = Aib [2-Aminoisobutyric acid]
SITE                  13
                      note = MISC_FEATURE - Xaa = Aib (2-Aminoisobutyric acid)
SITE                  39
                      note = MISC_FEATURE - Ser at position 39 is amidated as a
                       C-terminal primary amide
SITE                  20
                      note = MISC_FEATURE - Side chain amino (Epsilon amino)
                       group of Lys is substituted source
REGION                1..39
                      note = Synthetic
SEQUENCE: 13
YXEGTFTSDY SIXLDKIAQK AFVQWLIAGG PSSGAPPPS                          39
```

What is claimed is:

1. A polypeptide comprising the amino acid sequence:

(SEQ ID NO: 3)
Y-X1-E-G-T-F-T-S-D-Y-S-I-X2-L-D-K-I-A-Q-X3-A-F-V-

Q-W-L-X4-A-G-G-P-S-S-G-A-P-P-P-S, or a pharmaceutically acceptable salt thereof, wherein:

X1 is Aib or (L)-norvaline;

X2 is Leu or (L)-norvaline;

X3 is Lys, wherein the side chain amino (ε-amino) group of the Lys is acylated with a moiety having the formula:

{——U—W—Y—Z, wherein:

U is —C(O)—$CH_2$—O—$(CH_2)_2$—O—$(CH_2)_2$—NH—}, wherein} is point of attachment to W;

W is —C(O)—$C(CH_3)_2$—NH—], wherein] is point of attachment to Y;

Y is —C(O)—$(CH_2)_2$—CH(COOH)NH—, wherein — is point of attachment to Z; and

Z is —C(O)—$(CH_2)_n$—COOH or —C(O)—$(CH_2)_n$—$CH_3$, wherein n is an integer from 14 to 20;

X4 is Ile; and the acid group of the C-terminal amino acid is a free carboxylic acid group or is amidated as a C-terminal primary amide.

2. The polypeptide according to claim 1, wherein X1 is Aib.

3. The polypeptide according to claim 2, wherein Z is —C(O)—$(CH_2)_n$—COOH and n is 16 or 18.

4. The polypeptide according to claim 1, wherein X1 is (L)-norvaline.

5. The polypeptide according to claim 4, wherein Z is —C(O)—$(CH_2)_n$—COOH and n is 16 or 18.

6. The polypeptide according to claim 1, wherein X2 is Leu.

7. The polypeptide according to claim 6, wherein Z is —C(O)—$(CH_2)$n-COOH and n is 16 or 18.

8. The polypeptide according to claim 1, wherein X2 is (L)-norvaline.

9. The polypeptide according to claim 8, wherein Z is —C(O)—$(CH_2)_n$—COOH and n is 16 or 18.

10. The polypeptide according to claim 1, wherein X1 is Aib and X2 is Leu.

11. The polypeptide according to claim 10, wherein Z is —C(O)—$(CH_2)_n$—COOH and n is 16 or 18.

12. The polypeptide according to claim 1, wherein X1 is Aib and X2 is (L)-norvaline.

13. The polypeptide according to claim 12, wherein Z is —C(O)—$(CH_2)_n$—COOH and n is 16 or 18.

14. The polypeptide according to claim 1, wherein X1 is (L)-norvaline and X2 is Leu.

15. The polypeptide according to claim 14, wherein Z is —C(O)—$(CH_2)_n$—COOH and n is 16 or 18.

16. The polypeptide according to claim 1, wherein X1 is (L)-norvaline and X2 is (L)-norvaline.

17. The polypeptide according to claim 16, wherein Z is —C(O)—$(CH_2)_n$—COOH and n is 16 or 18.

18. The polypeptide according to claim 1, wherein Z is —C(O)—$(CH_2)_n$—COOH and n is 16 or 18.

19. The polypeptide according to claim 1, wherein the polypeptide comprises the amino acid sequence selected from the group consisting of:

(SEQ ID NO: 4)
i.) Tyr Aib Glu Gly Thr Phe Thr Ser Asp Tyr Ser

Ile L-norvaline Leu Asp Lys Ile Ala Gln Lys

Ala Phe Val Gln Trp Leu Ile Ala Gly Gly Pro

Ser Ser Gly Ala Pro Pro Pro Ser-$NH_2$;

(SEQ ID NO: 6)
ii.) Tyr Aib Glu Gly Thr Phe Thr Ser Asp Tyr Ser

Ile Leu Leu Asp Lys Ile Ala Gln Lys Ala Phe

Val Gln Trp Leu Ile Ala Gly Gly Pro Ser Ser

-continued

```
      Gly Ala Pro Pro Pro Ser-NH2;
      and
                                        (SEQ ID NO: 7)
iii.) Tyr L-norvaline Glu Gly Thr Phe Thr Ser Asp

      Tyr Ser Ile L-norvaline Leu Asp Lys Ile Ala
```

-continued

```
Gln Lys Ala Phe Val Gln Trp Leu Ile Ala Gly

Gly Pro Ser Ser Gly Ala Pro Pro Pro Ser-NH2.
```

20. The polypeptide according to claim 1, wherein {—U—W—Y—Z represents Moiety A or Moiety B, and wherein Moiety A and Moiety B have the following structures, respectively:

Moiety A

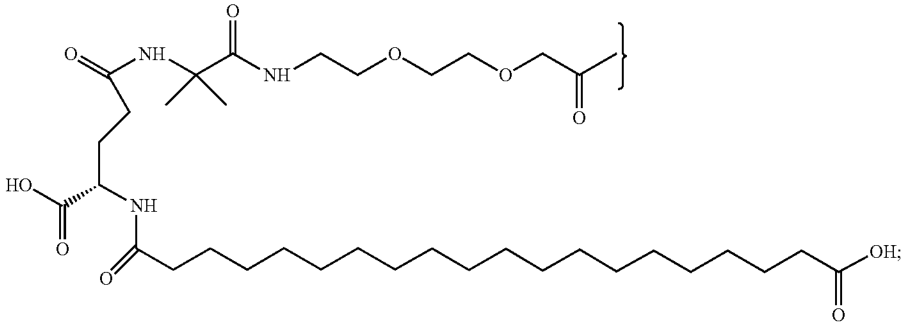

and

Moiety B

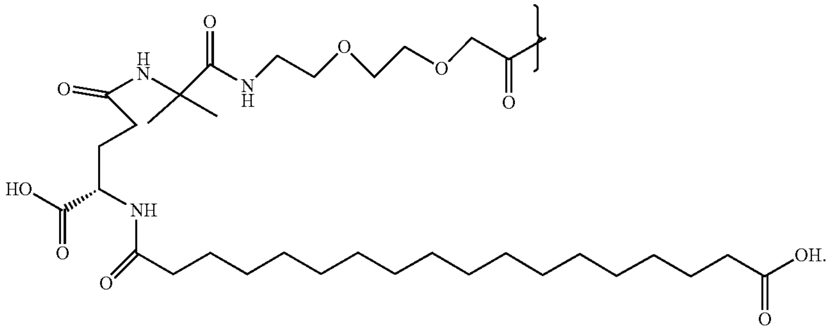

21. The polypeptide according to claim 1, wherein the C-terminal amino acid is amidated as a C-terminal primary amide.

22. The polypeptide according to claim 1, wherein the C-terminal amino acid is a free carboxylic acid.

23. A pharmaceutical composition comprising a polypeptide according to claim 1, and one or more of a pharmaceutically acceptable carrier, diluent, or excipient.

24. A polypeptide selected from the group consisting of:

(SEQ ID NO: 4)

Compound 1

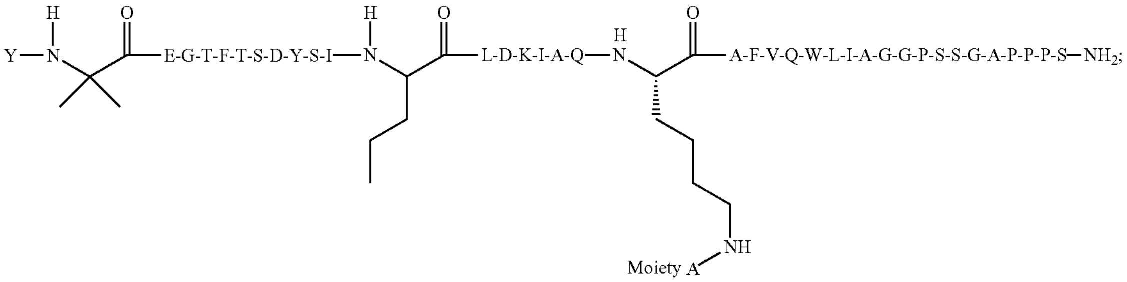

-continued
(SEQ ID NO: 6)
Compound 3
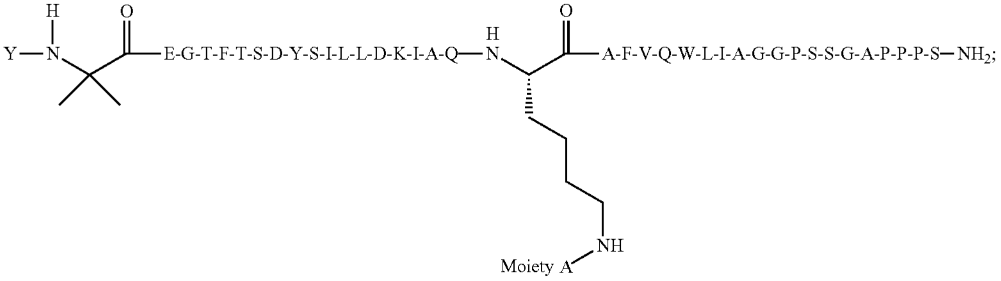
(SEQ ID NO: 7)
Compound 4
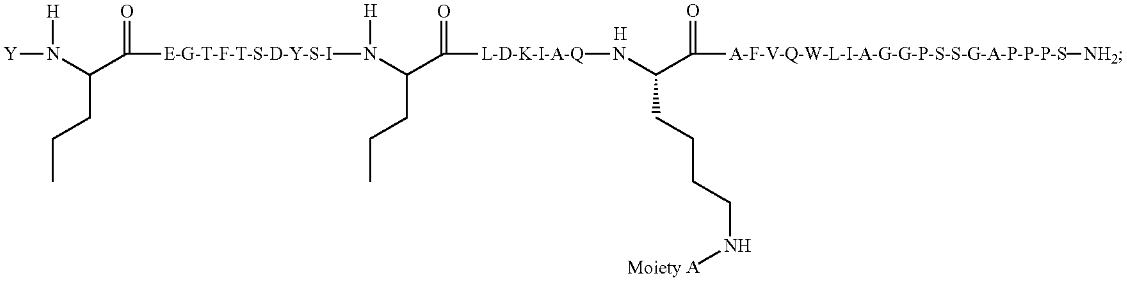
and
(SEQ ID NO: 4)
Compound 7
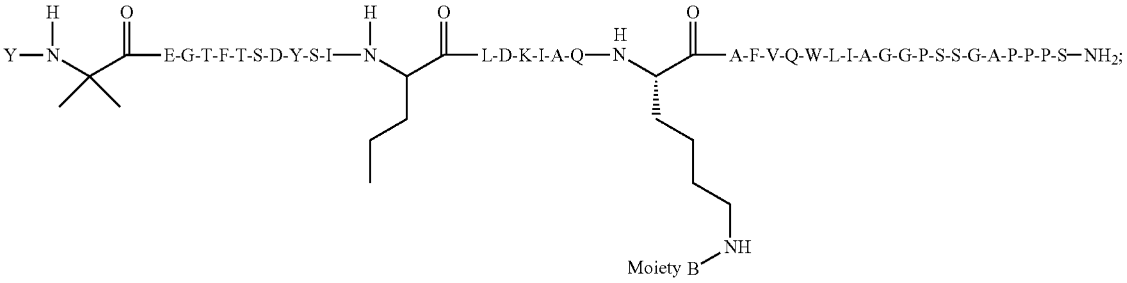
or a pharmaceutically acceptable salt thereof;
wherein:
Moiety A is
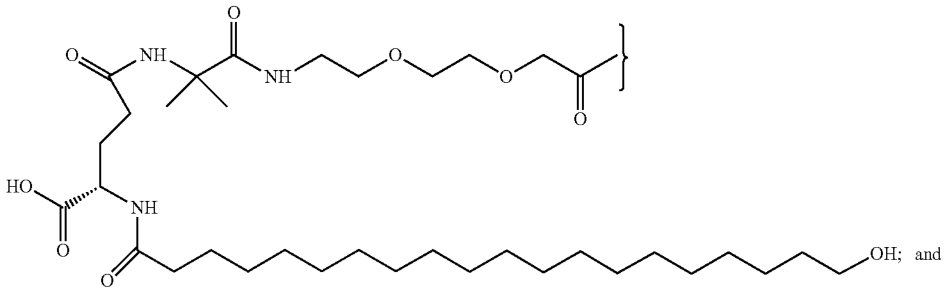
and -continued
Moiety B is 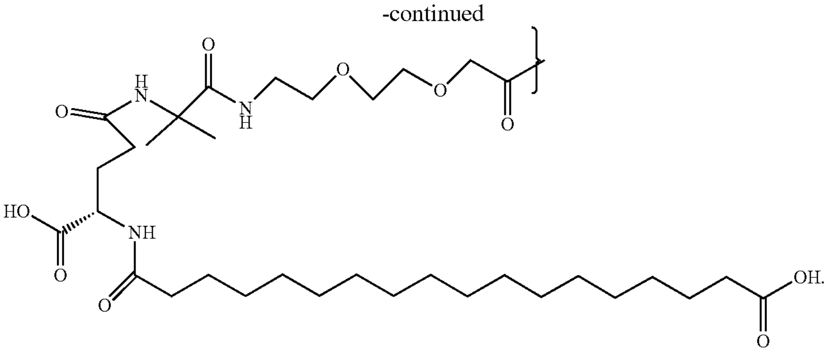
* * * * *